US010856478B2

(12) United States Patent
Sherlock et al.

(10) Patent No.: US 10,856,478 B2
(45) Date of Patent: Dec. 8, 2020

(54) APPARATUSES, METHODS, AND SYSTEMS FOR CULTIVATING A MICROCROP INVOLVING A FLOATING COUPLING DEVICE

(71) Applicant: PARABEL LTD., Grand Cayman (KY)

(72) Inventors: Peter Sherlock, Rockledge, FL (US); Harvey Weaver, Fellsmere, FL (US); Matthew Van Ert, Vero Beach, FL (US)

(73) Assignee: PARABEL NUTRITION, INC., Vero Beach, FL (US)

( * ) Notice: Subject to any disclaimer, the term of this patent is extended or adjusted under 35 U.S.C. 154(b) by 729 days.

(21) Appl. No.: 15/179,745

(22) Filed: Jun. 10, 2016

(65) Prior Publication Data

US 2016/0360715 A1    Dec. 15, 2016

Related U.S. Application Data

(60) Provisional application No. 62/173,648, filed on Jun. 10, 2015.

(51) Int. Cl.
*A01G 33/00* (2006.01)
*A01G 31/02* (2006.01)
(Continued)

(52) U.S. Cl.
CPC ............ *A01G 31/02* (2013.01); *A01G 33/00* (2013.01); *C12M 21/02* (2013.01); *C12M 23/18* (2013.01);
(Continued)

(58) Field of Classification Search
CPC ........ A01G 33/00; A01G 31/02; A01G 31/00; A01G 2031/006
See application file for complete search history.

(56) References Cited

U.S. PATENT DOCUMENTS

| 296,200 A | 4/1884 | McCarty |
| 650,063 A * | 5/1900 | Kersten .................. F03B 17/02 |
| | | 415/202 |

(Continued)

FOREIGN PATENT DOCUMENTS

| CN | 101116986 | 2/2008 |
| CN | 101595943 | 12/2009 |

(Continued)

OTHER PUBLICATIONS

Supplementary European Search Report in European Patent Application No. 16808482.0, dated Feb. 21, 2019.
(Continued)

*Primary Examiner* — Kristen C Hayes
(74) *Attorney, Agent, or Firm* — Baker & McKenzie LLP

(57) ABSTRACT

The present disclosure relates, according to some embodiments, to apparatuses, methods, and systems for cultivating a microcrop involving a floating coupling device. More specifically, the present disclosure relates, in some embodiments, to apparatuses and methods for cultivating *Lemna* for extracting proteins and/or carbohydrate rich products. In some embodiments, a bioreactor system for culturing a microcrop may comprise: a bioreactor container configured to contain the aquatic species in sufficient growth medium to permit normal growth of the microcrop, at least one coupling device comprising a star, and a propulsion mechanism configured to apply sufficient force to the at least one coupling device to cause motion thereof.

22 Claims, 15 Drawing Sheets

(51) Int. Cl.
*C12M 1/00* (2006.01)
*C12M 1/06* (2006.01)
*C12M 1/33* (2006.01)
*F16L 55/07* (2006.01)

(52) U.S. Cl.
CPC ............ *C12M 27/02* (2013.01); *C12M 45/02* (2013.01); *F16L 55/07* (2013.01)

(56) References Cited

U.S. PATENT DOCUMENTS

| | | | |
|---|---|---|---|
| 2,522,513 | A | 9/1950 | Hemmeter |
| 2,827,454 | A | 3/1958 | Nord |
| 2,867,945 | A | 1/1959 | Gotaas et al. |
| 3,468,057 | A | 9/1969 | Buisson et al. |
| 3,499,687 | A | 3/1970 | Ellis |
| 3,674,501 | A | 7/1972 | Betz et al. |
| 3,704,041 | A | 11/1972 | Loveland et al. |
| 3,768,200 | A | 10/1973 | Klock |
| 3,839,198 | A | 10/1974 | Shelef |
| 3,930,450 | A | 1/1976 | Symons |
| 3,955,318 | A | 5/1976 | Hulls |
| 4,005,546 | A | 2/1977 | Oswald |
| 4,041,640 | A | 8/1977 | Itanami et al. |
| 4,066,633 | A | 1/1978 | Gastineau et al. |
| 4,077,158 | A | 3/1978 | England |
| 4,137,868 | A | 2/1979 | Pryor |
| 4,253,271 | A | 3/1981 | Raymond |
| 4,429,867 | A | 2/1984 | Barber |
| 4,516,528 | A | 3/1985 | Jones |
| 4,557,937 | A | 12/1985 | Bournier |
| 4,560,032 | A | 12/1985 | Imanaka |
| 4,604,948 | A | 8/1986 | Goldhahn |
| 4,668,387 | A * | 5/1987 | Davie ................ C02F 3/082 210/150 |
| 4,840,253 | A | 6/1989 | DiMaggio et al. |
| 4,910,912 | A | 3/1990 | Lowrey, III |
| 5,047,332 | A | 9/1991 | Chahal |
| 5,121,708 | A | 6/1992 | Nuttle |
| 5,171,592 | A | 12/1992 | Holtzapple et al. |
| 5,269,819 | A | 12/1993 | Porath |
| 5,527,456 | A | 6/1996 | Jensen |
| 5,659,977 | A | 8/1997 | Jensen et al. |
| 5,667,445 | A | 9/1997 | Lochtefeld |
| 5,704,733 | A | 1/1998 | de Greef |
| 5,941,165 | A | 8/1999 | Butte |
| 6,077,548 | A | 6/2000 | Lasseur et al. |
| 6,096,546 | A | 8/2000 | Raskin |
| 6,251,643 | B1 | 6/2001 | Hansen et al. |
| 6,348,347 | B1 | 2/2002 | Hirabayashi et al. |
| 6,370,815 | B1 * | 4/2002 | Skill ................ A01G 33/00 47/1.4 |
| 7,058,197 | B1 | 6/2006 | McGuire et al. |
| 7,215,420 | B2 | 5/2007 | Gellerman et al. |
| 7,674,077 | B2 | 3/2010 | Opatril |
| 7,687,261 | B2 * | 3/2010 | Hazlebeck ............ C12M 21/02 435/257.1 |
| 7,819,576 | B2 * | 10/2010 | Zeikus ................ B01F 3/04113 366/102 |
| 8,183,032 | B2 * | 5/2012 | Frank ................ C12M 21/02 435/257.1 |
| 8,245,440 | B2 | 8/2012 | Ryan et al. |
| 8,287,740 | B2 | 10/2012 | Newman et al. |
| 8,715,980 | B2 * | 5/2014 | Clarke ................ C12M 21/02 435/173.7 |
| 8,722,878 | B2 | 5/2014 | Raines et al. |
| 8,790,913 | B2 * | 7/2014 | Zeikus ................ B01F 3/04531 435/257.1 |
| 9,051,539 | B2 * | 6/2015 | Snyder ................ C12M 21/02 |
| 9,295,206 | B2 * | 3/2016 | Jovine ................ A01G 33/00 |
| 9,675,054 | B2 | 6/2017 | Grajcar et al. |
| 10,039,244 | B2 * | 8/2018 | Shoham ............ C12M 1/3446 |
| 2004/0030516 | A1 | 2/2004 | Dunhill et al. |
| 2004/0144025 | A1 | 7/2004 | Johnson Rutzke |
| 2005/0258083 | A1 * | 11/2005 | Miller .................... C02F 3/082 210/150 |
| 2006/0024689 | A1 | 2/2006 | Bleuart et al. |
| 2007/0048859 | A1 | 3/2007 | Sears |
| 2007/0151522 | A1 | 7/2007 | Brauman |
| 2008/0032349 | A1 | 2/2008 | Visckov et al. |
| 2008/0086937 | A1 * | 4/2008 | Hazlebeck ............ C12M 21/02 47/1.4 |
| 2008/0096267 | A1 | 4/2008 | Howard et al. |
| 2008/0155890 | A1 | 7/2008 | Oyler |
| 2009/0088757 | A1 | 4/2009 | Tulkis |
| 2009/0151240 | A1 | 6/2009 | Kayama et al. |
| 2009/0285642 | A1 | 11/2009 | De Greef |
| 2010/0028505 | A1 | 2/2010 | Katzke et al. |
| 2010/0041095 | A1 | 2/2010 | Zeikus |
| 2010/0151558 | A1 | 6/2010 | Alianell et al. |
| 2010/0162620 | A1 | 7/2010 | McCaffrey et al. |
| 2010/0281836 | A1 | 11/2010 | Vanhoute et al. |
| 2010/0325948 | A1 | 12/2010 | Parsheh et al. |
| 2011/0016773 | A1 | 1/2011 | Nichols et al. |
| 2011/0092726 | A1 | 4/2011 | Clarke |
| 2011/0172102 | A1 | 7/2011 | Jacob et al. |
| 2012/0009660 | A1 | 1/2012 | Pottathil et al. |
| 2012/0117869 | A1 | 5/2012 | Javan et al. |
| 2012/0171753 | A1 | 7/2012 | Ivry |
| 2012/0288917 | A1 | 11/2012 | Krenbrink et al. |
| 2012/0308989 | A1 | 12/2012 | Barclay et al. |
| 2013/0023044 | A1 | 1/2013 | Gleason |
| 2013/0183705 | A1 | 7/2013 | Barclay et al. |
| 2013/0192130 | A1 | 8/2013 | Eckelberry |
| 2013/0244309 | A1 * | 9/2013 | Singh ....................... C12N 1/02 435/257.1 |
| 2014/0023675 | A1 | 1/2014 | Lina et al. |
| 2014/0212955 | A1 | 7/2014 | Ploechinger |
| 2014/0221630 | A1 | 8/2014 | Olivier et al. |
| 2014/0338261 | A1 | 11/2014 | Sykes |
| 2014/0356496 | A1 | 12/2014 | Melnyczuk |
| 2015/0072400 | A1 | 3/2015 | Clarke |
| 2015/0275161 | A1 | 10/2015 | Gressel et al. |
| 2016/0030350 | A1 | 2/2016 | Muller |
| 2016/0288001 | A1 | 10/2016 | Johnson |
| 2016/0360715 | A1 | 12/2016 | Sherlock et al. |
| 2017/0223935 | A1 | 8/2017 | Behrens |
| 2018/0014486 | A1 | 1/2018 | Creechley et al. |
| 2018/0118595 | A1 | 5/2018 | Curry |

FOREIGN PATENT DOCUMENTS

| | | |
|---|---|---|
| CN | 101370574 A | 2/2012 |
| CN | 102448286 | 5/2012 |
| CN | 202960947 | 6/2013 |
| CN | 204092345 | 1/2015 |
| CN | 104413257 | 3/2015 |
| CN | 104126494 A | 4/2016 |
| DE | 4133920 | 11/1993 |
| EP | 0285195 | 10/1988 |
| EP | 0765599 | 4/1997 |
| FR | 2522479 | 9/1983 |
| JP | S52151199 | 12/1977 |
| JP | S54147650 | 11/1979 |
| JP | S54147650 A | 11/1979 |
| JP | 2004097021 | 4/2004 |
| JP | 2005007837 | 1/2005 |
| JP | 2011254724 A | 12/2011 |
| JP | 2013521808 A | 6/2013 |
| KR | 2020000018164 | 10/2000 |
| KR | 101153379 | 6/2012 |
| MX | 2011010995 | 1/2012 |
| NL | 20111038645 | 9/2012 |
| WO | 9105849 | 5/1991 |
| WO | 9818344 | 5/1998 |
| WO | 0145523 | 6/2001 |
| WO | 2002034755 | 5/2002 |
| WO | 03028432 | 4/2003 |
| WO | 2007109066 | 9/2007 |
| WO | 2008020457 | 2/2008 |
| WO | 2008033573 | 3/2008 |
| WO | 2010123943 | 10/2010 |
| WO | 2010144877 | 12/2010 |

(56) References Cited

FOREIGN PATENT DOCUMENTS

| WO | 2011044194 | 4/2011 |
|---|---|---|
| WO | 2011116252 | 9/2011 |
| WO | 2011156662 | 12/2011 |
| WO | 2014046543 | 3/2014 |

OTHER PUBLICATIONS

First Examination Report in Australian Patent Application No. 2016276974, dated Apr. 9, 2019.
Office Action, mailed in Chinese Patent Application No. 201610789415.0 dated Apr. 26, 2019.
Office action dated Jan. 6, 2020 in Chinese Patent Application No. CN201680047105.X.
International Search Report and Written Opinion dated Oct. 27, 2016 for PCT application No. PCT/US2016/037046.
Examination Report, mailed in related Chinese Patent Application No. 201080023569.X, dated Sep. 20, 2012.
Office Action, mailed in Brazilian Patent Application No. PI1015000-5, notification published Jan. 23, 2018.
Office Action mailed in Brazilian Patent Application No. PI1015000-5, dated Dec. 20, 2017.
International Search Report and Written Opinion of the International Searching Authority (US) in related International Application No. PCT/US2010/031811, dated Jun. 18, 2010.
International Preliminary Report on Patentability of the International Preliminary Examination Authority (US) in related International Application No. PCT/US2010/031811, dated Oct. 11, 2011.
Office Action received in Brazilian Patent Application No. PI1015000-5, notification published May 10, 2018.
Office Action, mailed in Chinese Patent Application No. 201610789415.0 dated Nov. 5, 2018.
International Search Report and Written Opinion of the International Searching Authority (US) in PCT International Application No. PCT/US2011/028911, dated Nov. 30, 2011.
Office Action in Mexican Patent Application No. MX/a/2014/010053, dated Feb. 13, 2017.
Office Action mailed in Malaysian Patent Application No. PI 2011005000 dated Jun. 30, 2015.
Extended Search Report in European Patent Application No. 11757038.2, dated Mar. 9, 2017.
Office Action in European Patent Application No. 11757038.2, dated Jul. 16, 2018.
Office Action in Australian Patent Application No. 2015255285, dated Mar. 3, 2017.
Preliminary Examination Report in Peruvian Patent Application No. 1563-2012, dated Apr. 17, 2017.
International Preliminary Report on Patentability of the International Preliminary Examination Authority in PCT International Application No. PCT/US2011/028911, dated Sep. 18, 2012.
Office Action in Canadian Patent Application No. 2793512, dated Mar. 28, 2013.
Office Action in Canadian Patent Application No. 2793512, dated Aug. 7, 2017.
Office Action in Indonesian Patent Application No. W00201204170, dated Sep. 29, 2017.
Office Action in Japanese Patent Application No. 2015-020932 dated Jan. 27, 2017.
Office Action in Japanese Patent Application No. 2015-020932 dated Dec. 5, 2017.
Office Action in Indian Patent Application No. 8902/DELNP/2012 dated Aug. 3, 2018.
Office Action in European Patent Application No. 11757038.2, dated Jan. 3, 2019.
International Preliminary Report on Patentability by the International Preliminary Examination Authority for International Application No. PCT/US2016/037097, dated Dec. 22, 2017.
International Search Report and Written Opinion of the International Searching Authority for PCT application No. PCT/US2016/037099, dated Oct. 5, 2016.
International Preliminary Report on Patentability by the International Preliminary Examination Authority (Korean Intellectual Patent Office) for International Application No. PCT/US2016/037099, dated Dec. 12, 2017.
Extended Search Report in European Patent Application No. 16808483.8, dated Dec. 21, 2018.
International Preliminary Report on Patentability by the International Preliminary Examination Authority (Korean Intellectual Patent Office) for International Application No. PCT/US2016/037046, dated Dec. 12, 2017.
International Preliminary Report on Patentability by the International Preliminary Examination Authority (Korean Intellectual Patent Office) for International Application No. PCT/US2016/041156, dated Jan. 18, 2018.
International Search Report and Written Opinion of the International Searching Authority (Korean Intellectual Patent Office) for corresponding PCT application No. PCT/US2016/046422, dated Nov. 10, 2016.
International Preliminary Report on Patentability by the International Preliminary Examination Authority (Korean Intellectual Patent Office) for International Application No. PCT/US2016/046422, dated Feb. 22, 2018.
International Search Report and Written Opinion of the International Searching Authority for PCT application No. PCT/US2016/051366, dated Dec. 22, 2016.
International Search Report and Written Opinion of the International Searching Authority for PCT application No. PCT/US2016/051380, dated Dec. 26, 2016.
Sogbesan, OA; "Utilization of Treated Duckweed Meal (*Lemna pausicostata*) as Plant Protein Supplement in African Mud Catfish (*Clarias gariepinus*) Juvenile Diets" Fisheries and Aquaculture Journal, vol. 6, Issue 4, ISSN: 2150-3508 FAJ, 2015.
Extended Search Report of European Patent Office in European Patent Application No. 16845295.1, dated Jan. 15, 2019.
Office Action, mailed in Indian Patent Application No. 8948/DELNP/2011 dated Apr. 11, 2018.
Office Action, mailed in Brazilian Patent Application No. PI1015000-5, dated Sep. 26, 2018.
Pedroni et al., A Proposal to Establish International Network on Biofixation of C02 and Greenhouse Gas Abatement with Microalgae, Journal of Energy and Environmental Research, vol. 1, No. 1, Nov. 2001.
http://www.aquaponics.net.au/sites1 O.html, Murray Hallam, Practical Aquaponics for Everyone, Wayback Machine Dec. 2008, 3 pages.
Http://jeremybiggs.wordpress.com/2008/1 0/28/duck-attack/, The Garden Pond Blog, Oct. 2008, 2 pages.
http://collections.infocollections.org/ukedu/en/d/Jii23we/9.1.html, Workshop to produce an Information Kit on Farmer-proven integrated agriculture-aquaculture technologies, IIRR; 1992, 10 pages.
Fasakin, E.A. "Nutrient quality of leaf protein concentrates produced from water fern {*Azolla africanna* Desv) and Duckweed {*Spirodela polyrrhiza* L. Schleiden)", Bioresource Technology., vol. 69, No. 2, Aug. 1, 1999 (Aug. 1, 1999), pp. 185-187.
Fowden, L. "The Composition of the Bulk Proteins of Chlorella" [online] Published Jun. 20, 1951. Retrieved fromInternet Jun. 1, 2017: <URL:https://www.ncbi.nlm.nih.gov/pmc/articles/PMC1197660/pdf/biochemj00910-0079.pdf>.
Bolenz, S. et al. "Treatments of Water Hyacinth Tissue to Obtain Useful Products", Biological Wastes, Amsterdam, NL, vol. 33, No. 4, Jan. 1, 1990 {Jan. 1, 1990), pp. 263-274.
Kindel, Paul K. et al. "Solubilization of pectic polysaccharides from the cell walls of Lemna minor and Apium graveolens", Phytochemistry, vol. 41, No. 3, Feb. 1, 1996 (Feb. 1, 1996), GB, pp. 719-723.
Byers, M. "The Amino Acid Composition of Some Leaf Protein Preparations" in IBP Handbook No. 20, Leaf Protein: Its agronomy, Preparation, Quality and Use. 1971, International Biological Programme pp. 95-115.
Kennedy, David "Leaf Concentrate: A Field Guide for Small Scale Programs". Leaf for Life, 1993.

(56) References Cited

OTHER PUBLICATIONS

Cheng et al., "Growing Duckweed to Recover Nutrients from Wastewaters and for Production of Fuel Ethanol and Animal Feed", Clean, vol. 37, No. 1, pp. 17-26 (2009).
International Search Report and Written Opinion of the International Searching Authority (Korean Intellectual PatentOffice) for International Application No. PCT/US2016/041156, dated Oct. 18, 2016.
International Search Report and Written Opinion of the International Searching Authority (Korean Intellectual Patent Office) for corresponding PCT application No. PCT/US2016/037097 dated Nov. 10, 2016.
Freidig et al., Variation in Oxalic Acid Content among Commercial Table Beet Cultivars and Related Crops. Journal of the American Society for Horticultural Science, vol. 136, No. 1, pp. 54-60 (2011).
Extended Search Report in European Patent Application No. 16835862.0, dated Nov. 9, 2018.
Mazen, Ahmed M.A., "Calcium oxalate formation in Lemna minor: physiological and ultrastructural aspects of high capacity calcium sequestration" New Phytologist vol. 161, pp. 435-448, 2003.
International Preliminary Report on Patentability by the International Preliminary Examination Authority (Korean Intellectual Patent Office) for International Application No. PCT/US2016/051366, dated Mar. 22, 2018.
International Preliminary Report on Patentability by the International Preliminary Examination Authority (Korean Intellectual Patent Office) for International Application No. PCT/US2016/051380, dated Mar. 13, 2018.
Titi Mutiara K. et al., 'Effect of blanching treatments against protein content and amino acid drumstick leaves (*Moringa oleifera*)', Journal of Food Research, vol. 2, No. 1, pp. 101-108 (2013).
Gert Jan Schaafsma, 'Advantages and limitations of the protein digestibility-corrected amino acid score (PDCAAS)as a method for evaluating protein quality in human diets', British Journal of Nutrition, vol. 108, pp. S333-S336 (2012).
Extended Search Report in European Patent Application No. 16845285.2 dated Jan. 15, 2019.
Watson, Elaine, "Ultra-fast-growing aquatic plant promises year-round supply of sustainable vegetable protein", Jul. 24, 2015, p. 1-4, XP055537613, www.bakeryandsnacks.com, Retrieved from Internet: URL: www.bakeryandsnacks.com/Article/2015/07/06/Aquatic-plant-promises-year-round-supply-of-sustainable-plant-protein. [Retrieved from Internet on Dec. 21, 2018].
Extended Search Report in European Patent Application No. 16808454.9 dated Feb. 6, 2019.
Kwag, J.H. et al. "Conditions for artificial culture of Lemna Paucicostata and potentiality as an alternative biomass source"; J.Lives.House & Env. 16 (2) pp. 143-152, 2010.
Lentein, "Clean. Green. Protein", Retrieved from: https://web.archive.org/web/20150901074209/https://lentein.com, web accessed on Jul. 17, 2020.
Lentein, "Green Protein Powder", Retrieved from: https://web.archive.org/web/20150822012645/https://lentein.com/lentein-plus-powder, web accessed on Jul. 17, 2020.
Office Action, mailed in Japanese Patent Application No. 2018-516396, dated Jun. 2, 2020.
Office Action, mailed in Japanese Patent Application No. 2018-516401, dated Jun. 2, 2020.
Office Action, mailed in Japanese Patent Application No. 2018-532528, dated Jun. 23, 2020.

\* cited by examiner

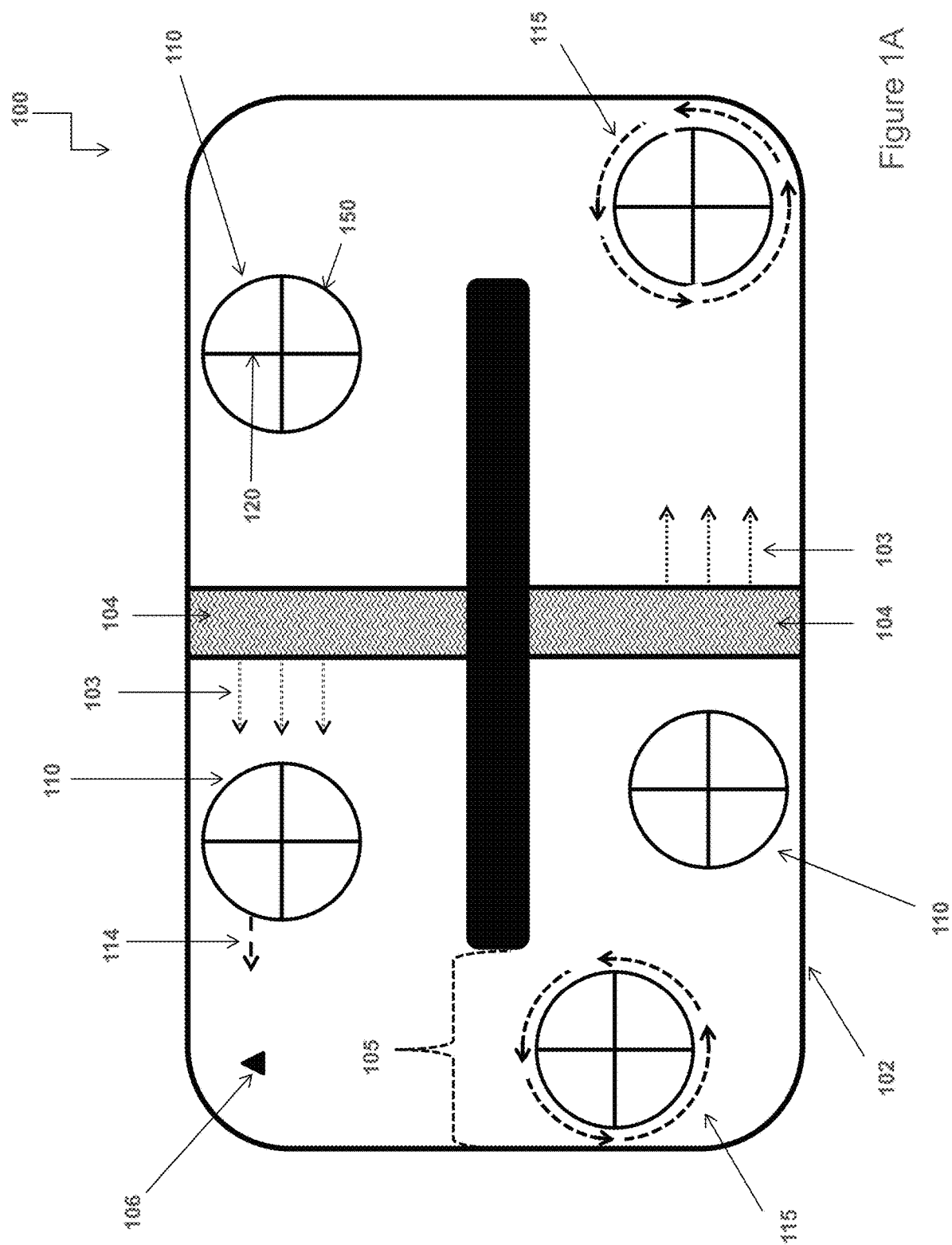

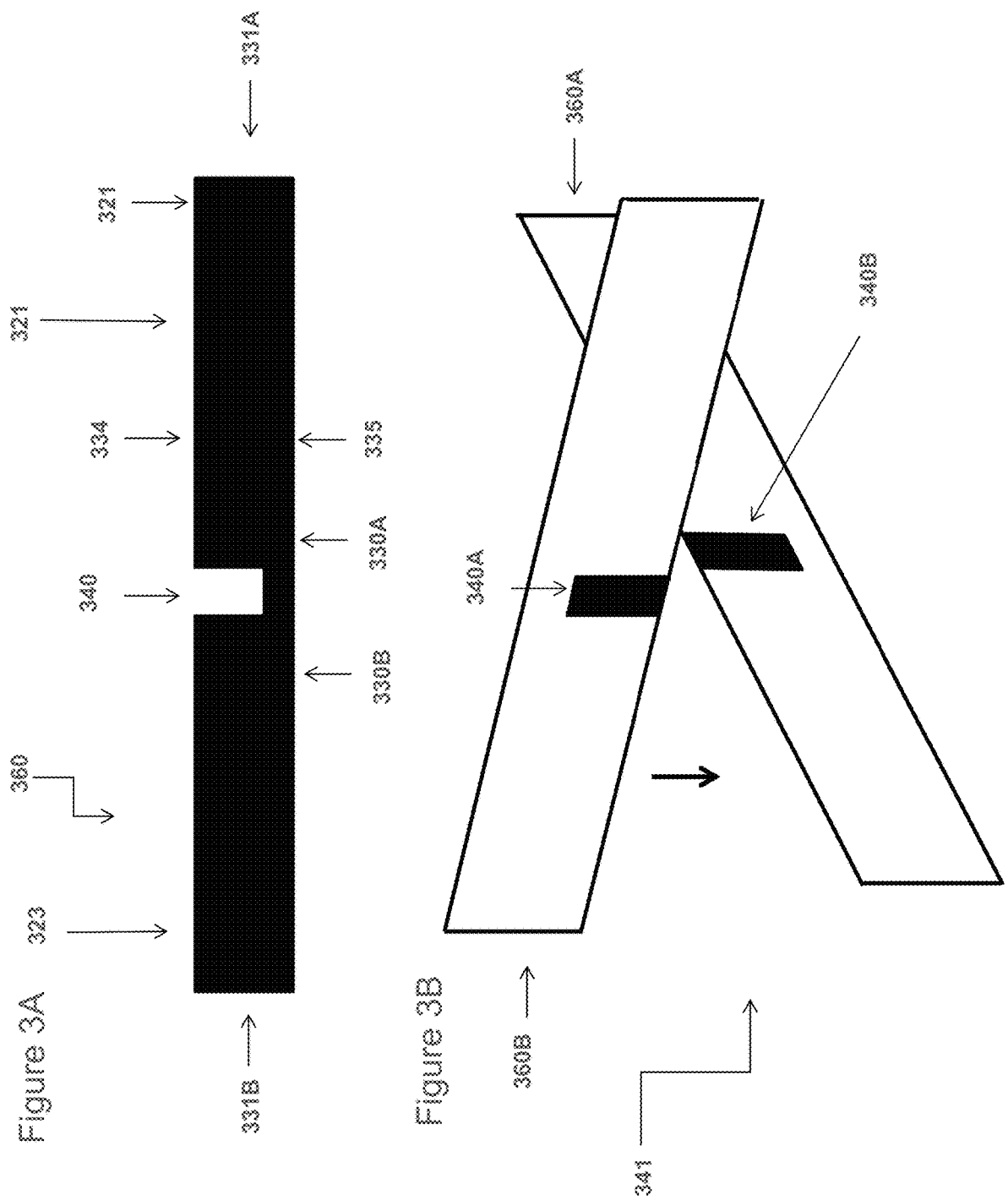

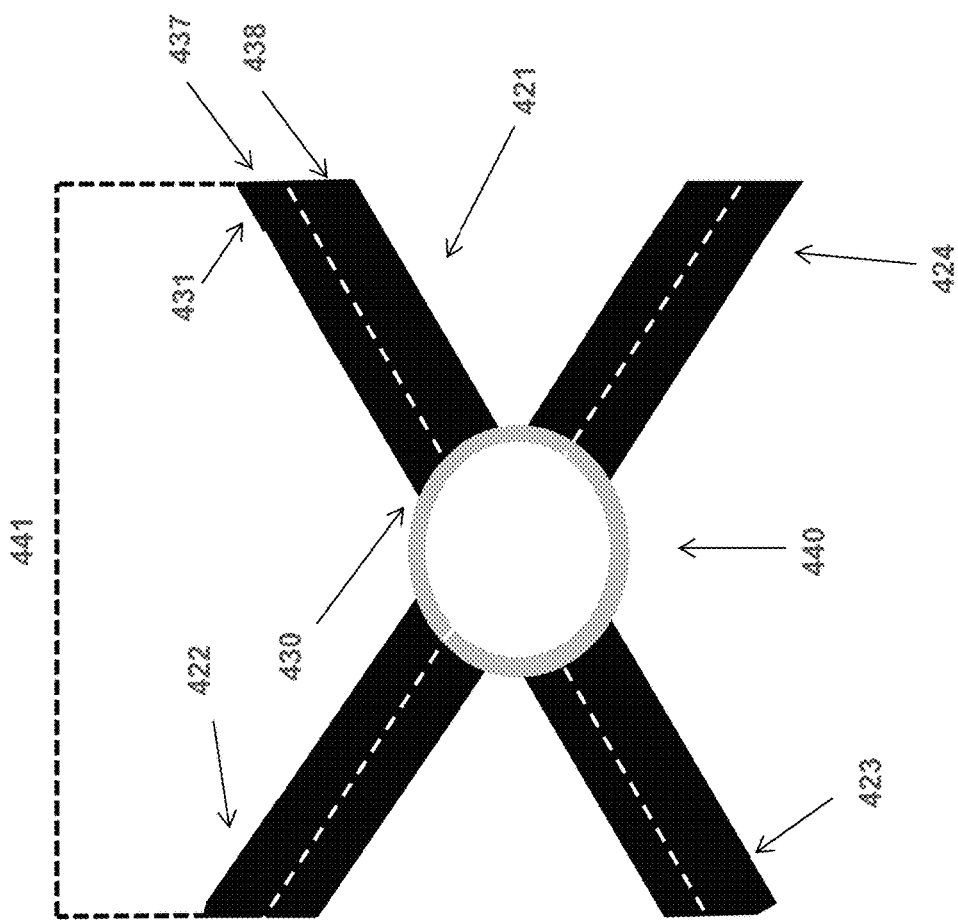

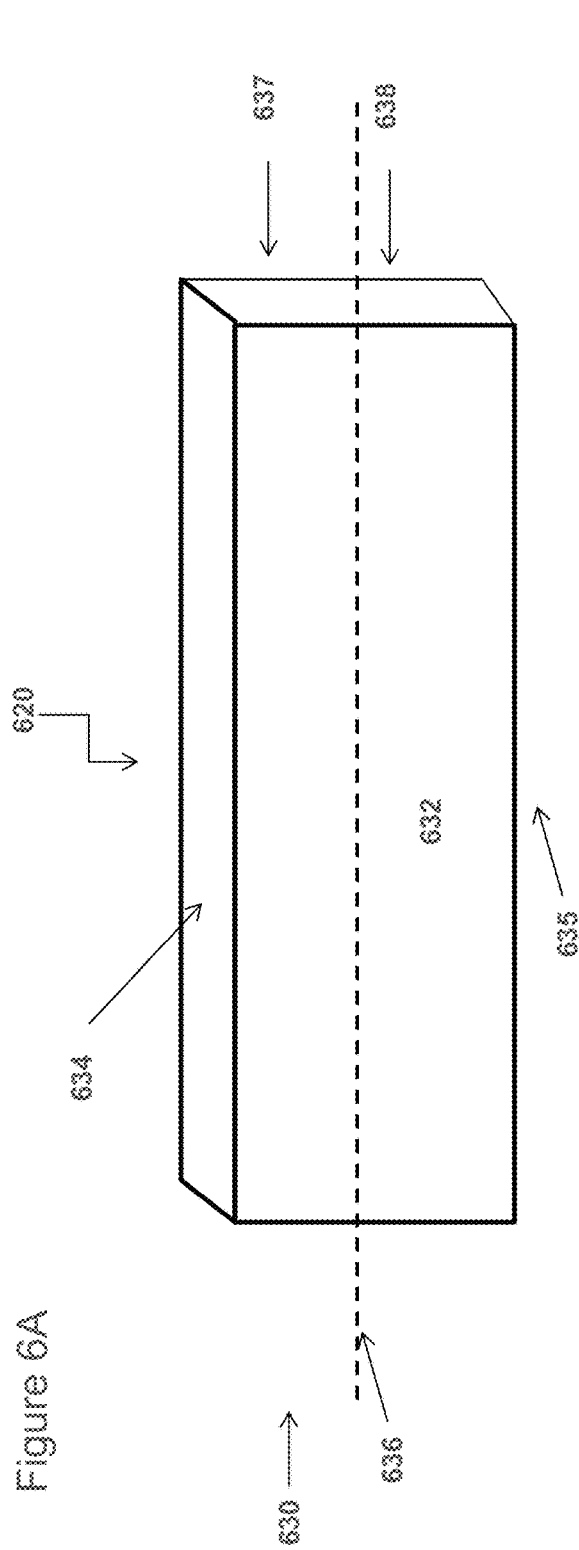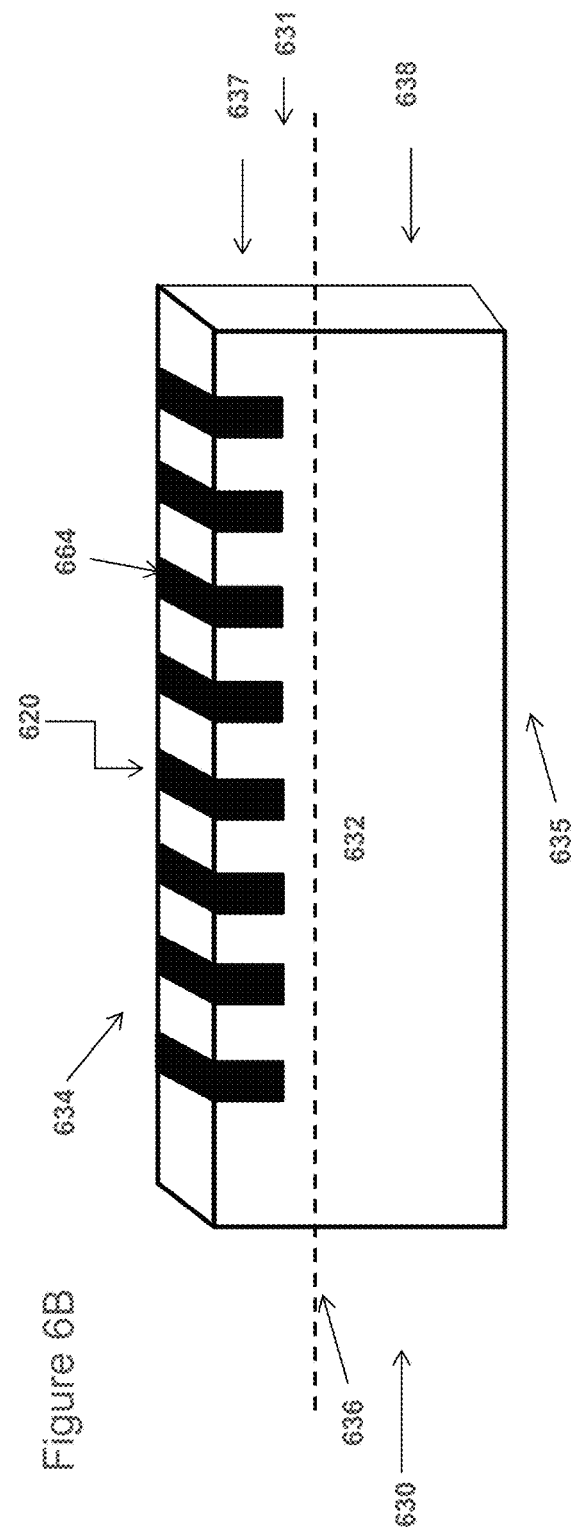

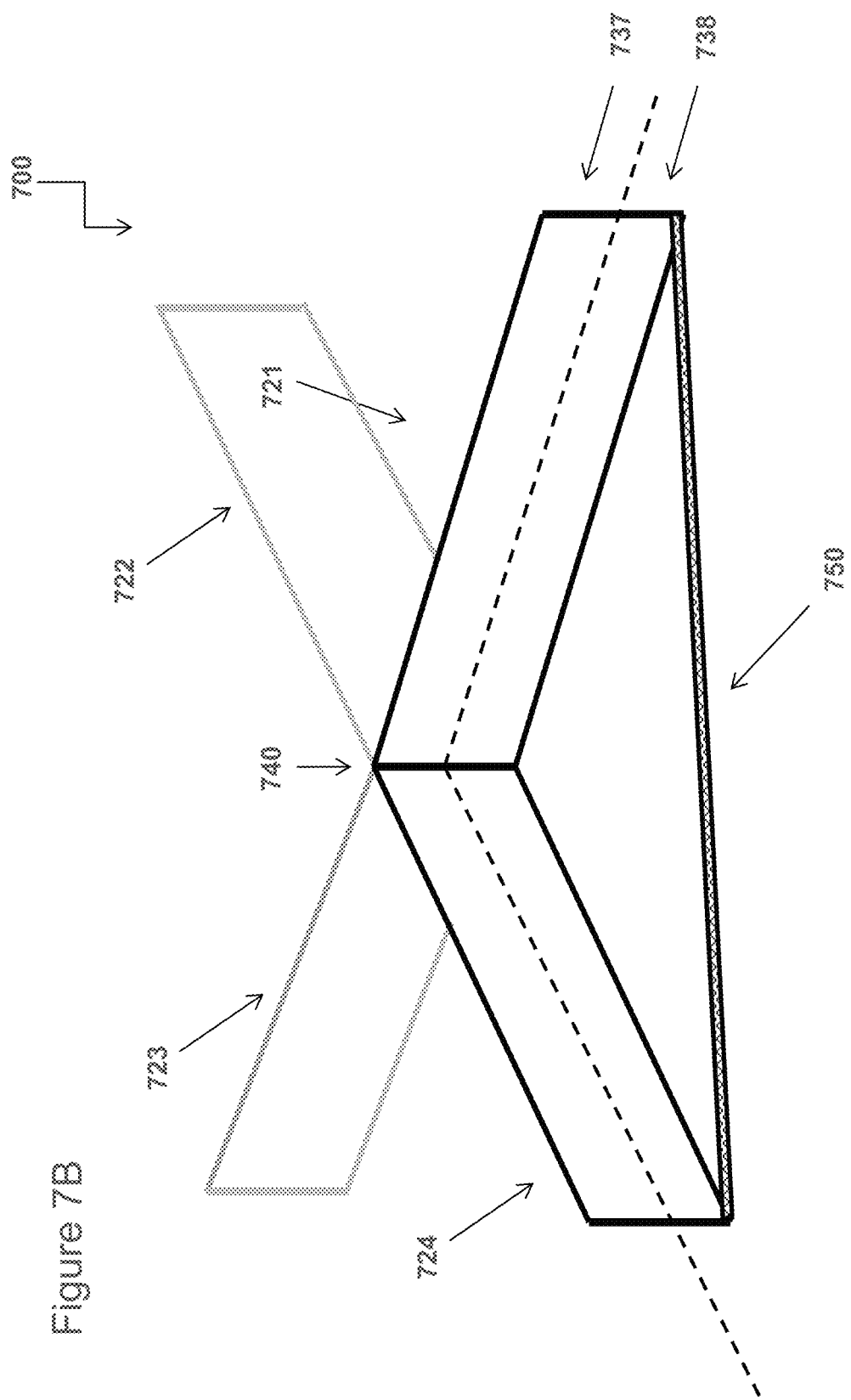

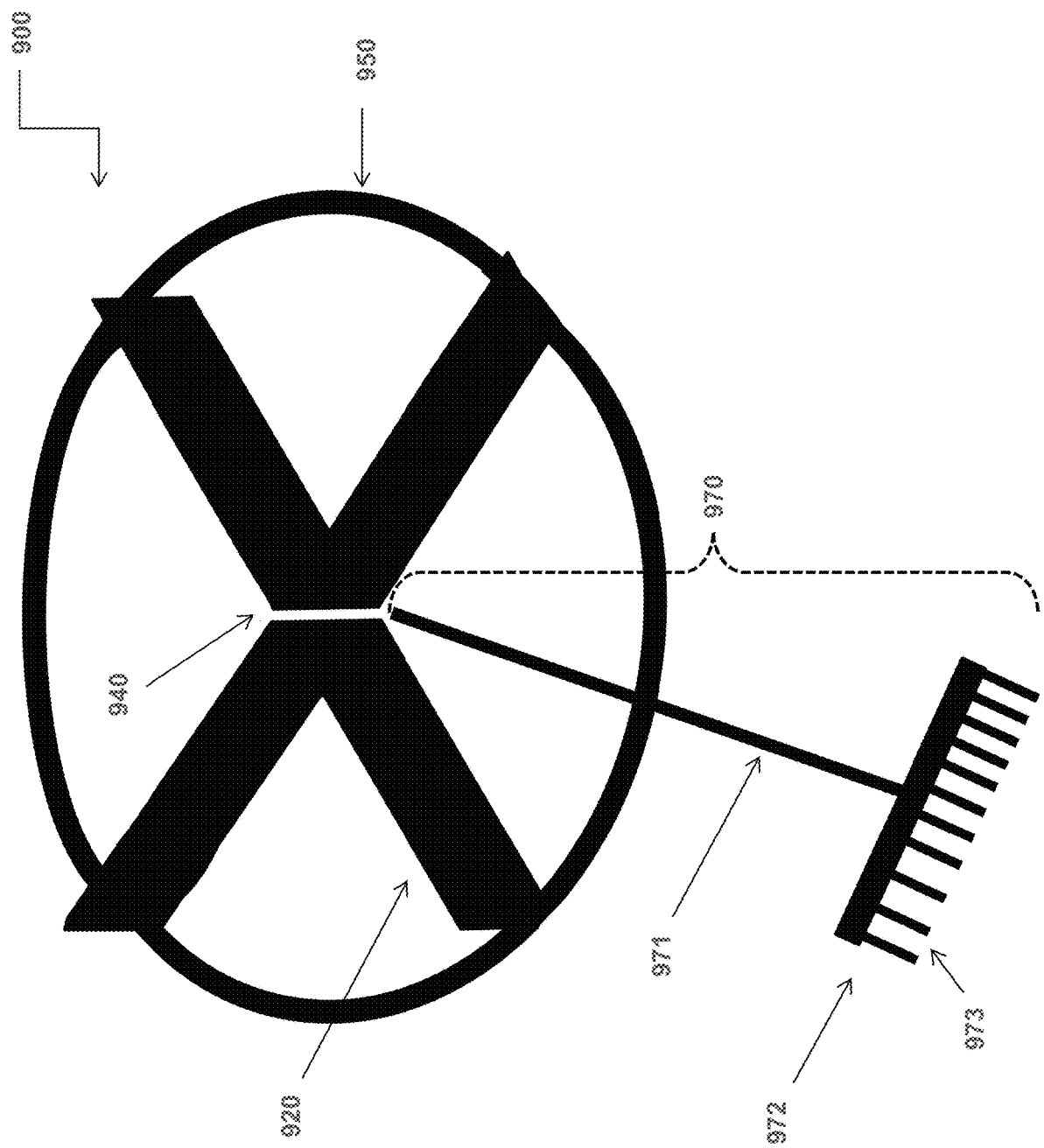

APPARATUSES, METHODS, AND SYSTEMS FOR CULTIVATING A MICROCROP INVOLVING A FLOATING COUPLING DEVICE

CROSS-REFERENCE TO RELATED APPLICATIONS

This application claims the benefit of U.S. Provisional Patent Application No. 62/173,648 filed on Jun. 10, 2015 which is incorporated herein by reference in its entirety as set forth in full.

FIELD OF THE DISCLOSURE

The present disclosure relates, in some embodiments, to apparatuses, methods, and systems for cultivating a microcrop involving a floating coupling device. More specifically, the present disclosure relates, in some embodiments to apparatuses and methods for cultivating *Lemna* to obtain proteins and/or carbohydrate rich products.

BACKGROUND OF THE DISCLOSURE

Floating microcrops (e.g., aquatic plant species, *Lemna*, algal species) are a valuable source of protein (e.g., for feed animals and human consumption), carbohydrates, and/or fuel feedstocks. Wind may alter the distribution of a floating microcrop on a surface of a growth medium causing, for example, the floating microcrop to pile on itself creating a mat with variable thickness. Piling of a floating microcrop may create microenvironments in which nutrients and other resources are limited or unevenly distributed, thus causing individual members of the floating microcrop to compete for resources (e.g., nutrients, sunlight, carbon dioxide, oxygen) thereby limiting population growth and yield.

In some cases, wind may alter the distribution of a mat of floating microcrop such that sunlight is capable of penetrating a surface of a liquid growth medium through openings in the mat. Sunlight penetrating through openings in a floating microcrop mat may support the growth of unwanted organisms in a liquid growth medium (e.g., phytoplankton, epiphytic algae). This may be particularly undesirable in commercial growth applications where nutrient-rich media exposed to sunlight may provide favorable growth conditions for unwanted organisms (e.g., phytoplankton, epiphytic algae). Such undesirable organisms may alter the chemical characteristics of the liquid growth media and/or compete with a floating microcrop for resources (e.g., nutrients, sunlight, carbon dioxide, oxygen) thereby limiting population growth and yield.

Increased flow of a liquid growth medium may offset the impact of wind and result in a more uniform distribution of a mat of floating microcrop. However, increasing flow of a liquid growth medium may undesirably increase energy requirements and/or costs.

SUMMARY

Accordingly, a need has arisen for improved apparatuses, methods, and systems for cultivating a microcrop in a more uniformly distributed culture.

The present disclosure relates, according to some embodiments, to apparatuses, methods, and systems for cultivating a microcrop in a uniformly or substantially uniformly distributed culture. For example, a bioreactor system for culturing an aquatic species may comprise: (1) a bioreactor container configured to contain the aquatic species in sufficient growth medium to permit normal growth of the aquatic species, (2) at least one coupling device comprising a star, and (3) a fluid conveyance mechanism configured to apply sufficient force to the at least one coupling device to cause motion thereof. In some embodiments, the at least one coupling device may further comprise a support band. According to some embodiments, a fluid conveyance mechanism may comprise a filter mechanism configured to remove at least a portion of a particulate matter from a growth medium.

In some embodiments, a coupling device may comprise a star. A coupling device, according to some embodiments, may be configured to move in response to a propulsion stream. According to some embodiments, a coupling device may comprise a star and a support band.

According to some embodiments, a star may comprise a plurality of arms joined at a connection point. For example, a star may comprise a first arm, a second arm, a third arm, and a fourth arm joined at a connection point and spaced 90° apart. A connection point may be a point in space or a hub, in some embodiments. A star, according to some embodiments, may comprise a plurality of blades joined at a connection point with each blade comprising a first arm joined to a second arm.

In some embodiments, a support band may comprise wood, plastic, polystyrene, metal, a composite, a resin, a laminate, particle board, plywood, mesh, chicken wire, ribbed aluminum, foam board, corrugated plastic board, woven fabric, wire, rope, string, or any combination thereof.

According to some embodiments, a coupling device may comprise at least one disruptor. Some embodiments of the disclosure relate to methods of assembling a coupling device. A method may comprise, for example, joining at least a first end of a first blade to a first end of a second blade at a connection point to form a star; connecting a first portion of the support band to at least a portion of a second end of the first blade; and connecting a second portion of the support band to at least a portion of a second end of the second blade. In some embodiments, a method of assembling a coupling device may further comprise attaching a disruptor to at least one of a first end of a first blade, a second end of the first blade, a first end of a second blade, a second end of the second blade, and a support band.

The disclosure, in some embodiments, relates to a method of cultivating a substantially uniformly distributed microcrop. For example, a method may comprise, growing a microcrop in a bioreactor system where the bioreactor system may comprise: (1) a bioreactor container configured to contain a microcrop in sufficient growth medium to permit normal growth of the microcrop; (2) at least one coupling device comprising a star; and (3) a fluid conveyance mechanism configured to apply sufficient force to the at least one coupling device to cause motion thereof. In some embodiments, a coupling device may further comprise a support band.

According to some embodiments, a microcrop may be *Lemna*.

BRIEF DESCRIPTION OF THE DRAWINGS

Some embodiments of the disclosure may be understood by referring, in part, to the present disclosure and the accompanying drawings, wherein:

FIG. 1A illustrates an aerial view of a bioreactor system configured for cultivating a microcrop, according to one embodiment of the disclosure;

FIG. 3A illustrates a perspective view of a blade, according to one embodiment of the disclosure;

FIG. 3B illustrates a perspective view of a method of assembling a star comprising a first blade and a second blade, according to one embodiment of the disclosure.

FIG. 4B illustrates a perspective view of a star, according to one embodiment of the disclosure;

FIG. 6A illustrates a perspective view of an arm, according to one embodiment of the disclosure;

FIG. 6B illustrates a perspective view of an arm, according to one embodiment of the disclosure;

FIG. 7B illustrates a perspective view of a coupling device, according to one embodiment of the disclosure;

FIG. 9A illustrates an aerial view of a coupling device including a disruptor, according to a specific embodiment of the disclosure.

DETAILED DESCRIPTION

Figure 1B:
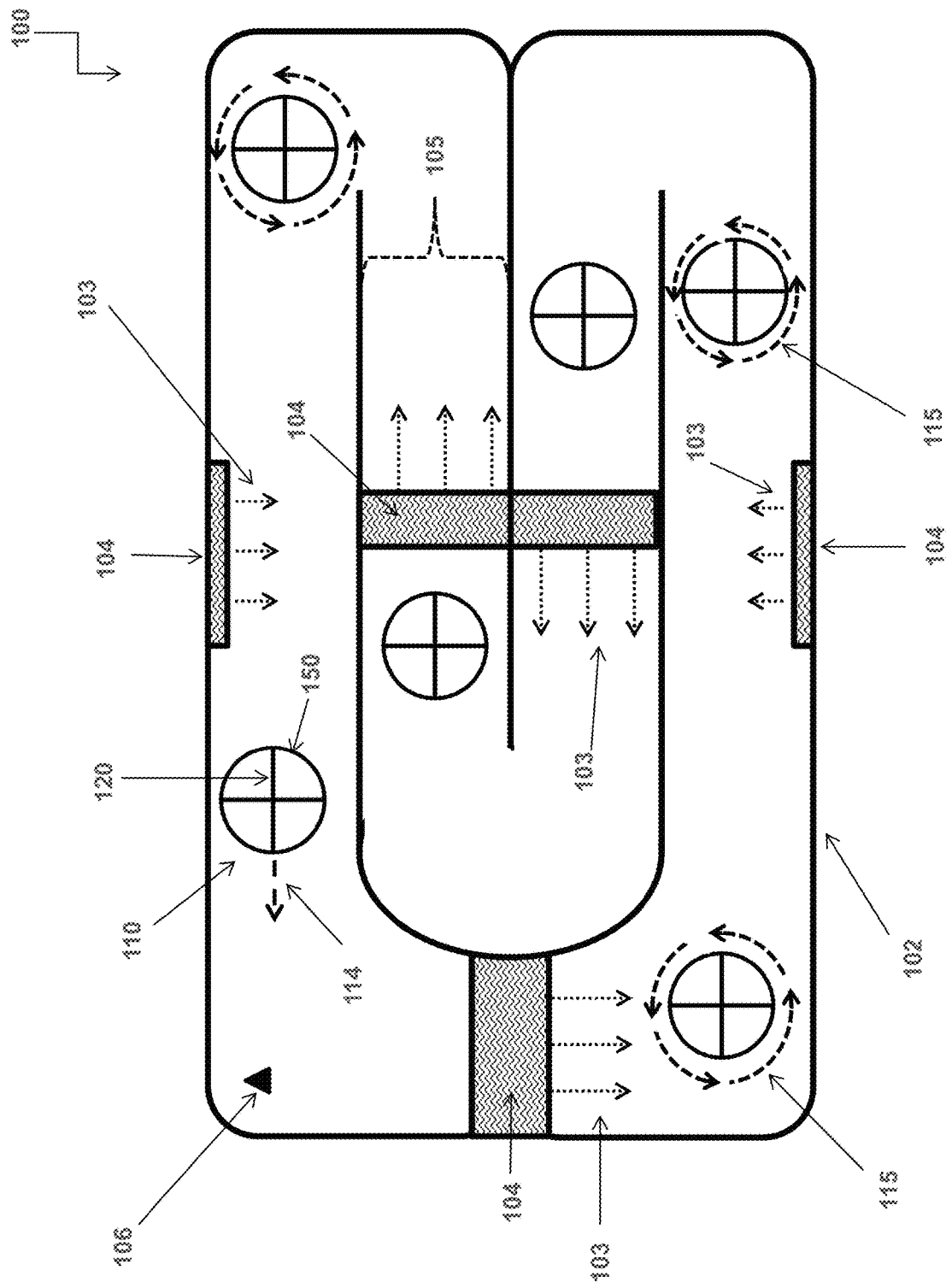
FIG. 1B illustrates an aerial view of a bioreactor system configured for cultivating a microcrop, according to one embodiment of the disclosure.

The present disclosure relates to apparatuses, methods, and systems for cultivation of a microcrop (e.g., aquatic plant species, *Lemna*, algal species). A cultivated microcrop may be processed to produce a protein concentrate (e.g., soluble protein, dry protein concentrate) and/or carbohydrate-rich products.

Microcrop

A microcrop (e.g., *Lemna*), according to some embodiments, may be capable of floating on the surface of a growth medium (e.g., water). In some embodiments, a microcrop may develop a floating mat on a surface of a growth medium that may increase in thickness as the microcrop population increases. According to some embodiments, a microcrop may comprise a single photosynthetic aquatic species (e.g., *Lemna* species, *Salvinia* species). A microcrop may include species of *Lemna* (e.g., duckweed), *Spirodela, Landoltia, Wolffiella, Salvinia* (e.g., floating fern), *Wolffia* (e.g., watermeal), *Azolla* (e.g., mosquito fern), *Pistia* (e.g., water lettuce), or any combination thereof. A microcrop may comprise, according to some embodiments, a combination of two or more photosynthetic aquatic species. In some embodiments, a microcrop may be selected from a local photosynthetic aquatic species based on identified compositional and growth characteristics that have developed within the local environmental conditions. Local species may out-compete other species in open ponds or bioreactors based on their adaptation to local environmental conditions. A microcrop, in some embodiments, may be adjusted in response to seasonal variations in temperature and light availability. A microcrop, in some embodiments, may have very short roots protruding into a growth medium allowing the microcrop to be easily blown across a surface of the growth medium by wind.

A microcrop may have characteristics that are advantageous in comparison to other photosynthetic aquatic species (e.g., rapid growth rate; reduced nutritional requirements; ease of harvesting and/or processing; enhanced amino acid profile; enhanced palatability; reduced evapotranspiration rate; increased protein composition).

For example, *Lemna* is a genus of free-floating aquatic plants from the Lemnaceae family (e.g., duckweed) that grow rapidly. *Lemna* protein has an essential amino acid profile that more closely resembles animal protein than most other plant proteins. Additionally, *Lemna* provides high protein yields, with freshly harvested *Lemna* containing up to about 43% protein by dry weight. Furthermore, compared with most other plants, *Lemna* leaves have a low fiber content (e.g., about 5%-about 15% in dry matter) and are highly digestible, even for monogastric animals. This contrasts with the compositions of many crop species (e.g., soy beans, rice, maize) which have fiber contents of approximately 50% and low digestibility.

Cultivation of a Microcrop

A microcrop may be cultivated in a bioreactor system, according to some embodiments. A bioreactor system, in some embodiments, may include a bioreactor container, a growth medium, one or more fluid conveyances (e.g., pump, jet, or other apparatus configured to accelerate a fluid), and one or more coupling devices. According to some embodiments, a bioreactor system may further include a monitoring system.

A Bioreactor Container

A bioreactor system may include, in some embodiments, a single bioreactor container in which a microcrop may be cultivated. In some embodiments, a bioreactor system may include multiple bioreactor containers that may be connected, partially connected, or disconnected. A bioreactor system, in some embodiments, may be configured to divide a bioreactor container(s) into channels or cells. For example, a bioreactor container may include one, two, three, four, five, six, seven, eight, nine, ten, or more than ten channels or cells. In some embodiments a bioreactor container may be divided into channels or cells by one or more partitions (e.g., a wall). A partition may have any appropriate dimensions. In some embodiments, a partition may be configured to redirect a flow of a growth medium within a bioreactor container. According to some embodiments, a partition may be configured to float on a surface of a growth medium within a bioreactor container and may be configured to redirect a flow of at least one of a microcrop and at least one coupling device (e.g., without redirecting a general flow of a growth medium, while minimally disturbing a general flow of a growth medium). A partition may be configured to extend from or across any surface of a bioreactor container (e.g., from a bottom surface to above a growth medium line; from a side surface part-way across a channel; from a bottom surface partially up a depth of a growth surface). According to some embodiments, a bioreactor system may be configured such that a microcrop biomass may be conveyed (e.g., propelled or impelled by underwater jets, bubbler, paddle wheel, and/or an axial/centrifugal mixer) in one or more bioreactor containers. A bioreactor system may be configured such that a microcrop biomass travels in a continuous loop, according to some embodiments.

According to some embodiments, a bioreactor may be configured as a raceway (e.g., FIG. 1A, 102). A bioreactor container may be configured as one or more serpentine raceways (e.g., FIG. 1B, 102), in some embodiments, with each of the serpentine raceways having a single channel or multiple channels. In some embodiments, a serpentine raceway may have multiple channels that are separated from one another, such that each raceway is configured for cultivating a separate microcrop biomass (e.g., a distinct microcrop in each channel, the same microcrop in each channel). A serpentine raceway bioreactor system may have multiple channels with the multiple channels being connected to one another in one or more locations such that a microcrop biomass may be conveyed through a connection point, for example, from a first raceway channel to a second raceway channel. According to some embodiments, a bioreactor system may be configured as a serpentine raceway with multiple channels and may have at least one variable connection point between at least a first channel and a second channel. A variable connection point may be configured to be opened (e.g., manually, automatically) such that a microcrop biomass may be conveyed through the variable connection point, in some embodiments. In some embodiments, a bioreactor system may be configured to allow one or more coupling devices to bypass a portion of the bioreactor system. For example, a bioreactor system may be configured with a channel that permits one or more coupling devices to flow through the channel and thereby bypass a fluid conveyance (e.g., paddle wheel).

In some embodiments a bioreactor container may have an area of ≥ about 0.1 hectares (ha), or ≥ about 0.2 ha, or ≥ about 0.3 ha, or ≥ about 0.4 ha, or ≥ about 0.5 ha, or ≥ about 1 ha, or ≥ about 1.5 ha, or ≥ about 2 ha, or ≥ about 2.5 ha, or ≥ about 3 ha, or ≥ about 3.5 ha, or ≥ about 4 ha, or ≥ about 4.5 ha, or ≥ about 5 ha, or ≥ about 5.5 ha, or ≥ about 6 ha, or ≥ about 6.5 ha, or ≥ about 7 ha, or ≥ about 7.5 ha, or ≥ about 8 ha, or ≥ about 8.5 ha, or ≥ about 9 ha, or ≥ about 9.5 ha, or ≥ about 10 ha. A bioreactor container may measure at least 10 meters long, or at least 20 meters long, or at least 50 meters long, or at least 100 meters long, or at least 150 meters long, or at least 200 meters long, or at least 250 meters long, or at least 300 meters long, or at least 350 meters long, or at least 400 meters long, or at least 450 meters long, or at least 500 meters long, or at least 600 meters long, or at least 700 meters long, or at least 800 meters long, in some embodiments.

According to some embodiments, a channel of a bioreactor container may be from about 0.5 meters (m) to about 50 m in width, or from about 1 m to about 40 m in width, or from about 3 m to about 30 m in width, or from about 4 m to about 25 m in width, or from about 5 m to about 20 m in width, or from about 6 m to about 18 m in width, or from about 7 m to about 15 m in width, or from about 8 m to about 15 m in width, or from about 9 m to about 12 m in width.

In some embodiments, a bioreactor container may be configured to hold a growth medium (e.g., water). A growth medium (e.g., water) in a bioreactor container, in some embodiments, may be at a depth of ≥1 cm, ≥2 cm, ≥3 cm, ≥4 cm, ≥5 cm, ≥10 cm, ≥15 cm, ≥20 cm, ≥25 cm, ≥30 cm, ≥35 cm, ≥40 cm, ≥45 cm, ≥50 cm, ≥60 cm, ≥70 cm, ≥80 cm, ≥90 cm, ≥100 cm, ≥110 cm, ≥120 cm, ≥130 cm, ≥140 cm, ≥150 cm, ≥160 cm, ≥170 cm, ≥180 cm, ≥190 cm, or ≥200 cm.

According to some embodiments, a bioreactor container may be embedded or partially embedded in a surface (e.g., an earthen surface). A bioreactor container (e.g., a serpentine raceway), in some embodiments, may be an earthen basin with one or more embankments (e.g., berms) made of compacted dirt (e.g., removed from the interior bottom of the bioreactor). In some embodiments, a bioreactor container may be mounted on a surface as an unexcavated ground structure. A bioreactor container, in some embodiments, may be an artificial container (e.g., metal, plastic, resin). According to some embodiments, a bioreactor container may comprise one or more peripheral walls comprising earth, metal, plastic, resin, concrete, or any combination thereof. In some embodiments, one or more peripheral walls may be reinforced with tension posts, wiring, Y-posts, Tee-posts, L-posts, and/or rebar. A bioreactor container, according to some embodiments, may be lined with a plastic liner (e.g., high density polyethylene (HDPE)).

In some embodiments a bioreactor system may be open (e.g., in a horizontal plane relative to the ground) such that a growth medium contained within a bioreactor container, a microcrop growing on a top surface of the growth medium, and/or a coupling device floating on a surface of the growth medium may be exposed to a wind initiating from an exterior of the bioreactor container. A bioreactor system, according to some embodiments, may be partially open (e.g., in a horizontal plane relative to the ground) such that at least 90% or at least 80%, or at least 70%, or at least 60%, or at least 50%, or at least 40%, or at least 30%, or at least 20%, or at least 10% of a growth medium contained within a bioreactor container, a microcrop growing on a top surface of the growth medium, and/or a coupling device floating on a surface of the growth medium may be exposed to a wind initiating from an exterior of the bioreactor container. A top surface may be open, according to some embodiments, where the surface is substantially free (e.g., free) of any covering or other barrier, where the surface is directly exposed to ambient weather conditions, where there is substantially no membrane, glass, cover or other barrier (whether or not such barrier has pores or apertures) between the surface and the atmosphere, where ambient atmosphere is the only occupant of the space immediately and directly above the surface for a distance of at least about 1 meter above the surface, and/or where ambient atmosphere is the only occupant of the space immediately and directly above the surface for a distance of at least about 1 meter above the surface, except for such portion of any microcrop or coupling device(s) present that protrudes above the surface.

In some embodiments, one or more peripheral walls of a bioreactor container may contain a wear strip. A wear strip may reduce or prevent wear caused by interactions between a coupling device and one or more peripheral walls. A wear strip may be removably or fixedly attached to one or more peripheral walls of a bioreactor container. According to some embodiments a wear strip may drape over one or more peripheral walls of a bioreactor container.

A Growth Medium

A bioreactor system may contain a growth medium. In some embodiments a growth medium may comprise water and/or a nutrient composition. A growth medium (e.g., water) may be provided in and/or added to a bioreactor container (e.g., serpentine raceway) and may be maintained at a desired set-point level (e.g., specific volume, specific depth), according to some embodiments. A bioreactor system, in some embodiments, may be configured to collect rainfall and/or to intake water from a source of ground, surface, or recycled water (e.g., storm water, recycled water) or any other suitable water source. According to some embodiments, a bioreactor system may further comprise an additional storage container (e.g., container or pond) for excess growth medium. A bioreactor system may be configured to insert additional nutrients (e.g., nitrogen, phosphorus, potassium) or gases (e.g., oxygen; carbon dioxide) into a growth medium (e.g., water) at specified time indicators or in response to sensor readings.

A Fluid Conveyance

A bioreactor system may be configured to permit a flow (e.g., active and/or passive flow) of growth medium, in some embodiments. In some embodiments, a bioreactor system may include a fluid conveyance. A fluid conveyance may comprise underwater jets, a bubbler, a recirculation system, a paddle wheel, an axial/centrifugal mixer, or any combination thereof. A bioreactor system, according to some embodiments, may be configured to adjust a flow rate of a growth medium (e.g., to redistribute nutrient concentrations or microcrop growth patterns).

A fluid conveyance, in some embodiments, may release a propulsion stream that may function to convey (e.g., propel and/or impel) a growth medium and/or a microcrop floating on a surface of the growth medium. According to some embodiments, a fluid conveyance may be configured to convey (e.g., propel or impel by underwater jets, bubbler, paddle wheel, and/or axial/centrifugal mixers) a growth medium and/or a biomass of a microcrop through a bioreactor container in a continuous loop at any desired velocity. For example, a fluid conveyance may be configured to move growth media at a velocity of about 0.01 m/s, or about 0.05 m/s, or about 0.1 m/s, or about 0.15 m/s, or about 0.2 m/s, or about 0.25 m/s, or about 0.3 m/s, or about 0.35 m/s, or about 0.4 m/s, or about 0.45 m/s, or about 0.5 m/s, or about 0.55 m/s, or about 0.6 m/s, or about 0.65 m/s, or about 0.7 m/s, or about 0.75 m/s, or about 0.8 m/s, or about 0.85 m/s, or about 0.9 m/s, or about 0.95 m/s, or about 1.0 m/s. A velocity or velocity range may be selected, according to some embodiments, in view of (e.g., as a function of) a number, density, size, and/or shape of coupling devices present and a quantity (e.g., speed, persistence) of wind blowing in the vicinity of a microcrop and thereby affecting the uniformity. Additionally, a velocity or velocity range may be selected according to a desired circulation time of a microcrop around a bioreactor container (e.g., a complete cycle through a serpentine raceway). An increased or decreased velocity and/or circulation time may be beneficial when harvesting a portion of a microcrop. Reciprocally, a number, density, size, and/or shape of coupling devices may be elected, according to some embodiments, in view of (e.g., as a function of) the operating and/or desired flow velocity necessary to maintain a uniform distribution of a microcrop (i.e., microcrop culture uniformity). Within a first velocity range, increasing a number, density, size, and/or shape of coupling devices may permit a flow (and corresponding energy requirements) to be reduced without loss or substantial loss of microcrop culture uniformity. Within a second velocity range (e.g., higher than the first range), increasing a number, density, size, and/or shape of coupling devices may further reduce an energy input required to maintain a desired flow velocity, so long as a packing density of the coupling devices in a bioreactor system is sufficient to permit movement (e.g., translation, rotation) without retarding a flow of a growth medium.

A fluid conveyance, in some embodiments, may be an underwater propulsion mechanism (e.g., underwater jets, bubbler, recirculation system, and/or axial/centrifugal mixers). According to some embodiments, a fluid conveyance may be situated at any point within a bioreactor container. A fluid conveyance, in some embodiments, may be situated on a bottom of a bioreactor container. In some embodiments, a fluid conveyance may be situated on one or more sides or peripheral walls of a bioreactor container. A fluid conveyance may extend across a channel in a bioreactor system, according to some embodiments. In some embodiments, a fluid conveyance may comprise a filter mechanism (e.g., an inline filter, a strainer) configured to remove suspended solids from a growth medium as the growth medium passes through the fluid conveyance.

According to some embodiments, a floating coupling device may increase an efficiency of an underwater propulsion mechanism in a bioreactor system by generating a positive displacement on a growth medium (i.e., a water column) as a result of one or more reactions forces that form as the coupling device is acted upon by the underwater propulsion mechanism In some embodiments a plurality of coupling devices may be immersed in a growth medium within a bioreactor system and spaced around the bioreactor system such that a plurality of positive displacements of a growth medium (i.e., the water column) may be generated. In some embodiments, a combination of a plurality of positive displacements on a growth medium column may be sufficient to generate a linear motor affect for propelling a growth medium.

In some embodiments, a microcrop may float at a surface of a growth medium and may resist movement more than a growth medium surrounding the microcrop. According to some embodiments, a microcrop may move in the same direction as a movement of a growth medium surrounding the microcrop. To convey (e.g., propel by underwater jets, bubbler, paddle wheel, and/or an axial/centrifugal mixers) a microcrop at a desired velocity a fluid conveyance may need to convey growth medium at a rate higher than the desired microcrop velocity, for example, when only a small surface area of a microcrop is present below a surface of the growth medium. A microcrop, according to some embodiments (e.g., under optimum nutrification conditions), may have very short roots extending into a growth medium and thereby may have a small surface area of the microcrop present below a surface of the growth medium.

A Coupling Device

According to some embodiments, a bioreactor system may include at least one coupling device. A bioreactor system, in some embodiments, may include a plurality of coupling devices.

A coupling device may be configured to transfer energy from a fluid conveyance (e.g., underwater jets, bubbler, paddle wheel, and/or axial/centrifugal mixers) to a microcrop floating on a surface of a growth medium, according to some embodiments. In some embodiments, transferring an energy from a fluid conveyance to a coupling device may initiate movement of the coupling device, for example, translation, rotation, or combinations thereof. Movement of a coupling device may redistribute a portion of a growth medium and/or a portion of a microcrop. According to some embodiments, movement of a coupling device may be at least one translation, counterclockwise or clockwise rotation, or a combination thereof. Movement of a coupling device, in some embodiments, may fluctuate between a counterclockwise rotation and a clockwise rotation. In some embodiments, each of a plurality of coupling devices may move independently, such that at a given point in time at least one of the plurality of coupling devices may rotate in a direction that is different than at least one other of the plurality of coupling devices. Movement, in some embodiments, may be translation of a coupling device from a first point to a second point.

According to some embodiments, movement of a coupling device (e.g., translation, rotation, tumbling) may be initiated and/or accelerated when a submerged portion of the coupling device (e.g., a bottom portion of at least one arm) contacts a moving fluid (e.g., a propulsion stream). Velocity of a coupling device movement, in some embodiments, may be about equal to a velocity of a growth medium column and/or a propulsion stream. In some embodiments, a bioreactor system may be configured such that a coupling device may redistribute a portion of a growth medium and/or a portion of a microcrop where a velocity of a growth medium column and/or a propulsion stream are ≤0.01 m/s, or ≤0.05 m/s, or ≤0.1 m/s, or ≤0.15 m/s, or ≤0.2 m/s, or ≤0.25 m/s, or ≤0.3 m/s, or ≤0.35 m/s, or ≤0.4 m/s, or ≤0.45 m/s, or ≤0.5 m/s, or ≤0.55 m/s, or ≤0.6 m/s, or ≤0.65 m/s, or ≤0.7 m/s, or ≤0.75 m/s, or ≤0.8 m/s, or ≤0.85 m/s, or ≤0.9 m/s, or ≤0.95 m/s, or ≤1.0 m/s.

A bioreactor system comprising at least one coupling device may be capable of maintaining a substantially uniform distribution (e.g., a uniform distribution) of a microcrop (e.g., with or without wind affects). In some embodiments, a bioreactor system comprising at least one coupling device may be capable of mitigating changes resulting from wind by maintaining a substantially uniform distribution (e.g., a uniform distribution) of a microcrop. By transferring energy from a fluid conveyance to a coupling device a bioreactor system may require less energy input (e.g., velocity) to maintain a uniform distribution of a microcrop on a surface of a growth medium (e.g., with or without wind). For example, a bioreactor reactor system subjected to a wind that requires a fluid conveyance at a first velocity to maintain a substantially uniform distribution (e.g., a uniform distribution), may be capable of maintaining the substantially uniform distribution of the microcrop at a second, lower velocity by incorporating at least one coupling device.

In some embodiments, a plurality of coupling devices may be adjusted (e.g., number, shape, composition of arms) based on environmental and production conditions (e.g., size of bioreactor container; growth medium velocity; energy availability; wind speed; growth medium composition).

According to some embodiments, a coupling device may be partially submerged in a growth medium within a bioreactor container. According to some embodiments, a percentage of a coupling device may be submerged when the coupling device is placed in a growth medium, providing a surface area sufficient to transfer energy from a fluid conveyance (e.g., underwater jets) to a microcrop floating on a surface of the growth medium. A coupling device, in some embodiments, may be configured such that ≥20%, or ≥30%, or ≥40%, or ≥50%, or ≥60%, or ≥70%, or ≥80%, or ≥90%, or ≥95%, or ≥98% of a cross-section of the coupling device is submerged when the coupling device is placed in a growth medium.

A coupling device, in some embodiments, may comprise a star. In some embodiments a coupling device may comprise a star and a support band (e.g., FIG. 2). A star may be formed by joining a plurality of arms at a connection point (e.g., point in space, hub), according to some embodiments. In some embodiments, a star may be formed by joining a plurality of blades with each blade comprising a first arm joined to a second arm.

A coupling device may have any desired dimensions and/or proportions. A coupling device may be formed of any desired materials and may be formed as a unitary whole or assembly of joined components. Components may be joined by any desired means including, for example, melt fusion, adhesion, bridle, finger, dado, dovetail, dowel, screw, bolt, and/or rivet joints. In some embodiments, one or more portions of a coupling device may have pores through which growth media may flow. A plurality of arms may be generally co-planar and/or generally uniformly distributed about a central axis. A support band may be generally planar. In some embodiments, a support band plane may be generally parallel to a plurality of arms plane.

According to some embodiments, a distal end of an arm may be configured to reduce or prevent wear of a peripheral wall of a bioreactor container resulting from interactions between one or more arms of a coupling device and the peripheral wall. In some embodiments configuring an arm to reduce or prevent wear of a peripheral wall may consist of smoothing a distal end of the arm or capping the distal end of the arm with a non-abrasive material.

A Star

According to some embodiments, a coupling device may be configured to have any desired shape, size, or composition. A coupling device may include, for example, a star with a regular and/or irregular geometric arrangement of lines that share a common point (e.g., vertex, hub) from which they extend and/or through which they pass. Each arm may have any desired shape (e.g., fin, blade, spoke) and may be the same or different shape from other arms of a star. Each arm of a star may be coplanar or generally coplanar with up to all of the other arms. Where arms have (or form) a fin or blade shape, a central longitudinal axis of each arm may be coplanar or generally coplanar with a central longitudinal axis of up to all of the other arms. A star may have a pattern of or resembling, for example, a wheel, a route, an asterisk, a cross, and/or a propeller. A star may include, according to some embodiments, any desired number of arms including odd or even numbers of arms. A star (e.g., FIG. 2, 241) may be formed by joining a plurality of arms at a connection point (e.g., hub), according to some embodiments. Each arm of a plurality of arms may have a first end, a second end, a first side, a second side, an upper side, and a lower side, according to some embodiments (e.g., FIG. 6A). A star may comprise any number of arms.

In some embodiments, a star may comprise a plurality of blades with each blade comprising a first arm joined to a second arm. A blade, in some embodiments, may be a single unit (e.g., molded or extruded out of plastic). A star may comprise any number of blades. In some embodiments, a blade may include a connection point (e.g., slot, screw hole) disposed between a first of a plurality of arms and a second of the plurality of arms. A first connection point of a first blade may be joined to a first connection point of a second blade to form a star, in some embodiments. In some embodiments, a first connection point of a first blade may be joined to a first connection point of a second blade and a first connection point of a third blade to form a star. A first connection point of a first blade may be joined, in some embodiments, to a first connection point of a second blade and a first connection point of a third blade and a first connection point of a fourth blade to form a star (e.g., a propeller).

A star, in some embodiments, may comprise at least a first arm, a second arm, and a third arm. According to some embodiments, a star may comprise at least a first arm, a second arm, a third arm, and a fourth arm. A star, in some embodiments, may comprise at least a first arm, a second arm, a third arm, a fourth arm, and a fifth arm. In some embodiments, a star may comprise at least a first arm, a second arm, a third arm, a fourth arm, a fifth arm, and a sixth arm. According to some embodiments, a star may comprise at least a first arm, a second arm, a third arm, a fourth arm, a fifth arm, a sixth arm, and a seventh arm. A star may comprise at least a first arm, a second arm, a third arm, a fourth arm, a fifth arm, a sixth arm, a seventh arm, and an eighth arm, in some embodiments.

According to some embodiments, a star may have a diameter such that a coupling device can freely translate and/or rotate within a bioreactor container without becoming lodged in place against one or more edges of the bioreactor container. In some embodiments, a star may have a diameter of about 0.2 m, or about 0.3 m, or about 0.4 m, or about 0.5 m, or about 0.6 m, or about 0.7 m, or about 0.8 m, or about 0.9 m, or about 1.0 m, or about 1.1 m, or about 1.2 m, or about 1.3 m, or about 1.4 m, or about 1.5 m, or about 1.6 m, or about 1.7 m, or about 1.8 m, or about 1.9 m, or about 2.0 m, or about 2.1 m, or about 2.2 m, or about 2.3 m, or about 2.4 m, or about 2.5 m, or about 2.6 m, or about 2.7 m, or about 2.8 m, or about 2.9 m, or about 3.0 m, or about 3.2 m, or about 3.4 m, or about 3.6 m, or about 3.8 m, or about 4.0 m, or about 4.2 m, or about 4.4 m, or about 4.6 m, or about 4.8 m, or about 5.0 m, or about 5.2 m, or about 5.4 m, or about 5.6 m, or about 5.8 m, or about 6.0 m.

Each of the plurality of arms, according to some embodiments, may have a length, measured from a first end to a second end, of about 0.1 m, or about 0.15 m, or about 0.2 m, or about 0.25 m, or about 0.3 m, or about 0.35, or about 0.4 m, or about 0.45 m, or about 0.5 m, or about 0.55 m, or about 0.6 m, or about 0.65 m, or about 0.75 m, or about 0.8 m, or about 0.85 m, or about 0.9 m, or about 1 m, or about 1.1 m, or about 1.2 m, or about 1.3 m, or about 1.4 m, or about 1.5 m, or about 1.6 m, or about 1.7 m, or about 1.8 m, or about 1.9 m, or about 2 m, or about 2.1 m, or about 2.2 m, or about 2.3 m, or about 2.4 m, or about 2.5 m, or about 2.6 m, or about 2.7 m, or about 2.8 m, or about 2.9 m, or about 3 m. In some embodiments, a first of a plurality of arms within a star may have a different length than a second of the plurality of arms and/or a third of the plurality of arms. A first of a plurality of arms within a star, may have a length equal to a second of the plurality of arms and a third of the plurality of arms, in some embodiments.

In some embodiments, a plurality of arms of a star may each have a height, measured from an upper side to a lower side, such that a coupling device can freely translate and/or rotate within a bioreactor container without becoming lodged or scraping (e.g., fouling) on a bottom of a bioreactor container or a fluid conveyance contained therein. Each of a plurality of arms, according to some embodiments, may have a height, measured from an upper side to a lower side, of $\geq 0.05$ cm, or $\geq 0.1$ cm, or $\geq 0.2$ cm, or $\geq 0.3$ cm, or $\geq 0.4$ cm, or $\geq 0.5$ cm, or $\geq 0.6$ cm, or $\geq 0.7$ cm, or $\geq 0.8$ cm, or $\geq 0.9$ cm, or $\geq 1$ cm, or $\geq 2$ cm, or $\geq 3$ cm, or $\geq 4$ cm, or $\geq 5$ cm, or $\geq 10$ cm, or $\geq 15$ cm, or $\geq 20$ cm, or $\geq 25$ cm, or $\geq 30$ cm, or $\geq 35$ cm, or $\geq 40$ cm, or $\geq 45$ cm, or $\geq 50$ cm, or $\geq 60$ cm, or $\geq 70$ cm, or $\geq 80$ cm, or $\geq 90$ cm, or $\geq 100$ cm, or $\geq 110$ cm, or $\geq 120$ cm, or $\geq 130$ cm, or $\geq 140$ cm, or $\geq 150$ cm, or $\geq 160$ cm, or $\geq 170$ cm, or $\geq 180$ cm, or $\geq 190$ cm, or $\geq 200$ cm. In some embodiments, a first of a plurality of arms within a star may have a different height than a second of the plurality of arms and/or a third of the plurality of arms. A first of a plurality of arms within a star, may have a height equal to a second of the plurality of arms and a third of the plurality of arms, in some embodiments. According to some embodiments, $\geq 20\%$, or $\geq 30\%$, or $\geq 40\%$, or $\geq 50\%$, or $\geq 60\%$, or $\geq 70\%$, or $\geq 80\%$, or $\geq 90\%$, or $\geq 95\%$, or $\geq 98\%$ of a height of each of a plurality of arms may be submerged when a coupling device is placed in a growth medium. In some embodiments, floats and/or weights may be attached to a coupling device such that a desired height of each of a plurality of arms may be submerged.

A plurality of arms of a star, in some embodiments, may each have a depth, measured from a first side to a second side. According to some embodiments, each of a plurality of arms may have a depth, measured from a first side to a second side, of $\geq 0.5$ mm, or $\geq 1$ mm, or $\geq 1.5$ mm, or $\geq 2$ mm, or $\geq 2.5$ mm, or $\geq 3$ mm, or $\geq 3.5$ mm, or $\geq 4$ mm, or $\geq 4.5$ mm, or $\geq 5$ mm, or $\geq 6$ mm, or $\geq 7$ mm, or $\geq 8$ mm, or $\geq 9$ mm, or $\geq 10$ mm, or $\geq 15$ mm, or $\geq 20$ mm, or $\geq 25$ mm, or $\geq 30$ mm, or $\geq 35$ mm, or $\geq 40$ mm, or $\geq 45$ mm, or $\geq 50$ mm. In some embodiments, a first of a plurality of arms within a star may have a different depth than a second of the plurality of arms and/or a third of the plurality of arms. A first of a plurality of arms within a star, may have a depth equal to a second of the plurality of arms and a third of the plurality of arms, in some embodiments.

In some embodiments, a first end of a plurality of arms may be connected to and extend from a connection point, to form a star. According to some embodiments, at least a first end of a first arm, a first end of a second arm, and a first end of a third arm may be connected to and extend from a connection point, to form a star. A star, in some embodiments, may have a first end of a first arm, a first end of a second arm, a first end of a third arm and at least one of a first end of a fourth arm, a first end of a fifth arm, a first end of a sixth arm, a first end of a seventh arm, and a first end of an eighth arm connected to and extending from a connection point.

Figure 2:
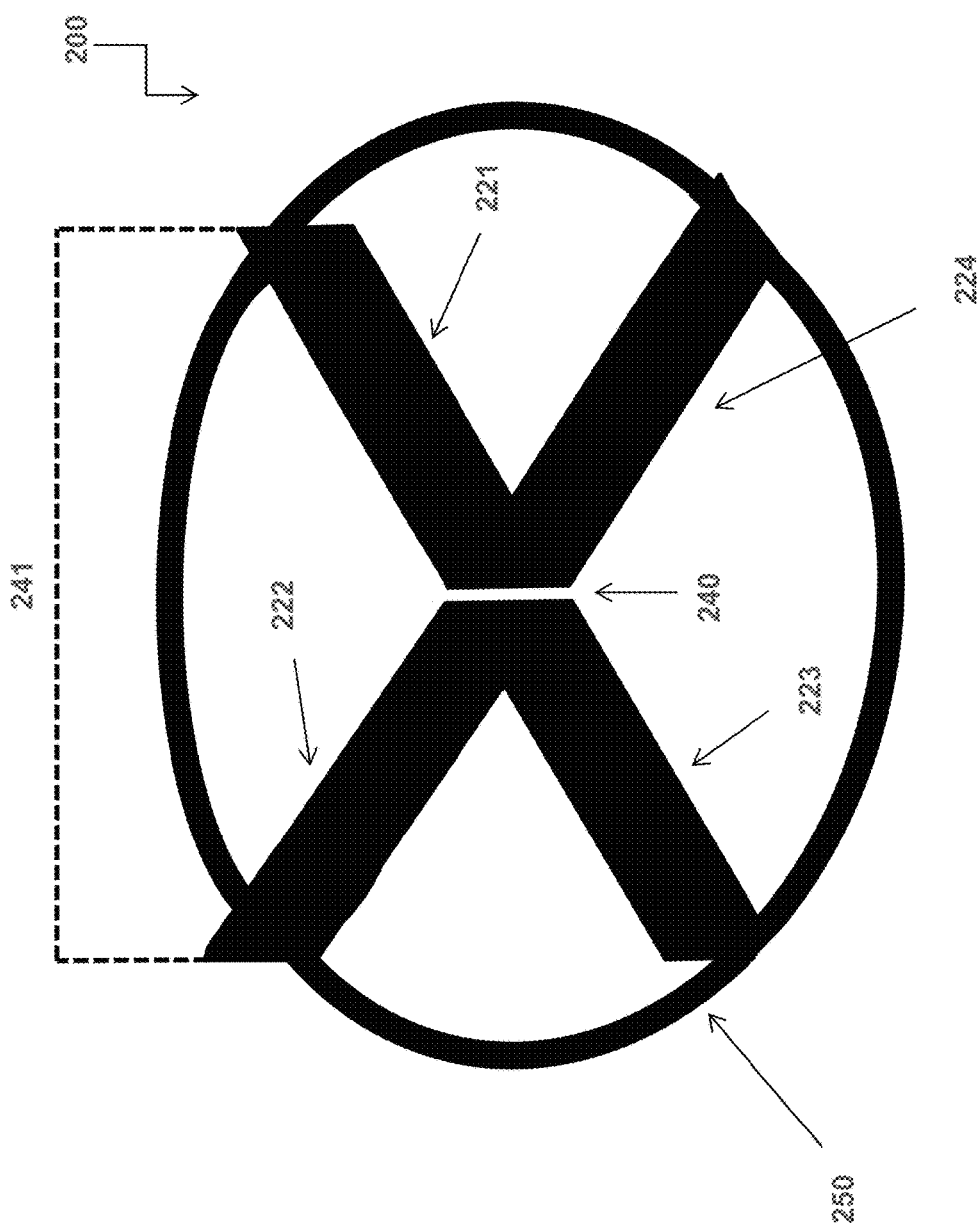
FIG. 2 illustrates a perspective view of a coupling device, according to one embodiment of the disclosure.

According to some embodiments, a connection point may be a common point in space where a first end of a plurality of arms are fixedly attached to one another such that a second end of each of the plurality of arms extend outward away from the connection point (e.g., FIG. 2). A second end of each of a plurality of arms, in some embodiments, may extend outward from a connection point such that the plurality of arms are in a single plane and parallel to an upper surface of a growth medium. A connection point may be a point of intersection between two intersecting lines and/or a connection point of three or more concurrent lines.

A connection point, in some embodiments may be a hub to which a first end of each of a plurality of arms may be fixedly connected. In some embodiments, a hub may be ring shaped or cylindrical (e.g., FIG. 4B). According to some embodiments, a hub may be fully (e.g. spherical, cube, cylindrical with a closed top and bottom) or partially enclosed (e.g., cylindrical with a closed top or bottom) with a hollow interior. A hub may include indentations, slots, or holes (e.g., threaded, unthreaded) in which a first end of a plurality of arms may be inserted. According to some embodiments, a hub may be configured such that a plurality of arms connect to the hub in a single plane with the single plane being parallel to an upper surface of a growth medium. A hub may be configured such that a first portion of a plurality of arms may be connected to the hub in a first plane and a second portion of the plurality of arms may be connected to the hub in a second plane, with both the first plane and the second plane being parallel to an upper surface of a growth medium.

According to some embodiments, a star may be configured with a plurality of arms equally spaced around a connection point (e.g., point in space, hub). For example, a star may be configured with three arms at 120° apart; or four arms at 90° apart; or five arms at 72° apart; or six arms at 60° apart; or seven arms at 51.4° apart; or eight arms at 45° apart. A star, in some embodiments, may be configured with a plurality of arms unequally spaced around a connection point. For example, a star may be configured with a first arm spaced 180° from a second arm and a third arm spaced 90° from the second arm (e.g., FIG. 8D).

A star, in some embodiments, may be configured such that when the star is immersed in a growth medium an upper side of a plurality of arms may be oriented to have any desired contact (e.g., angle, depth) with the growth media. For example, each arm independently may be oriented parallel to an upper surface (e.g., in a horizontal plane relative to the sky) of the growth medium. According to some embodiments, a star may be configured such that when immersed in a growth medium a second end of a first arm, a second end of a second arm, and a second end of a third arm independently may be oriented perpendicular to an upper surface (e.g., in a horizontal plane relative to the sky) of the growth medium. In some embodiments, a star may be configured such that when immersed in a growth medium a second end of a first arm, a second end of a second arm, and a second end of a third arm may be oriented at an angle relative to an upper surface (e.g., in a horizontal plane relative to the sky) of the growth medium. For example, a second end of a first arm may be oriented at an angle of about 85°, or about 80°, or about 75°, or about 70°, or about 65°, or about 60° relative to an upper surface (e.g., in a horizontal plane relative to the sky) of a growth medium.

In some embodiments, a star may be partially submerged in a growth medium such that at least one of a top portion of a first arm, a top portion of a second arm, a top portion of a third arm, a top portion of a fourth arm, a top portion of a fifth arm, a top portion of a sixth arm, a top portion of a seventh arm, and a top portion of an eighth arm may be protruding above a surface of the growth medium; and at least one of a bottom portion of the first arm, a bottom portion of the second arm, a bottom portion of the third arm, a bottom portion of the fourth arm, a bottom portion of the fifth arm, a bottom portion of the sixth arm, a bottom portion of a seventh arm, and a bottom portion of an eighth arm may be submerged below the upper surface of the growth medium (e.g., FIG. 6A). At least one of a top portion of a plurality of arms may be configured to separate or re-distribute a biomass of a microcrop, according to some embodiments. In some embodiments, at least one of a bottom portion of a plurality of arms may be configured to transfer an energy from a fluid conveyance to a coupling device.

In some embodiments, at least one of a top portion of a first arm, a top portion of a second arm, a top portion of a third arm, a top portion of a fourth arm, a top portion of a fifth arm, a top portion of a sixth arm, a top portion of a seventh arm, a top portion of an eighth arm, or any combination thereof may comprise any suitable material, including for example: wood, plastic, polystyrene, metal, a composite, a resin, a laminate, particle board, plywood, mesh, chicken wire, ribbed aluminum, foam board, corrugated plastic board, or any combination thereof. According to some embodiments, a composition of a top portion of a first arm, a top portion of a second arm, a top portion of a third arm, a top portion of a fourth arm, a top portion of a fifth arm, a top portion of a sixth arm, a top portion of a seventh arm, a top portion of an eighth arm, or any combination thereof may be selected to contribute to at least one of: (1) rigidity and/or resilience of at least one of a plurality of arms; (2) cost efficiency of a coupling device; or (3) a specific buoyancy of a coupling device. A top portion of a plurality of arms may be configured such that a growth medium and/or a microcrop may flow through portions of the top portion. According to some embodiments, a top portion of a plurality of arms may be configured to separate or re-distribute a biomass of a microcrop. For example, a top portion of a plurality of arms may be slotted (e.g., FIG. 6B) and/or contain holes (e.g., mesh) (e.g., FIG. 6C) such that a growth medium and/or portions of a biomass may flow through at least one slot and/or at least one hole. In some embodiments, a top portion of a plurality of arms may have at least one slot on an upper side of the plurality of arms (e.g., FIG. 6B). For example, a top portion of a plurality of arms may be slotted such that it resembles a comb or rake (e.g., FIG. 6B). A top portion of a plurality of arms may have slots within a body of the plurality of arms, according to some embodiments.

At least one of a bottom portion of a first arm, a bottom portion of a second arm, a bottom portion of a third arm, a bottom portion of a fourth arm, a bottom portion of a fifth arm, a bottom portion of a sixth arm, a bottom portion of a seventh arm, a bottom portion of an eighth arm, or any combination thereof may comprise any suitable material, including, for example: wood, plastic, polystyrene, metal, a composite, a resin, a laminate, particle boards, plywood, ribbed aluminum, foam board, corrugated plastic board, or any combination thereof. A composition of a bottom portion of a first arm, a bottom portion of a second arm, a bottom portion of a third arm, a bottom portion of a fourth arm, a bottom portion of a fifth arm, a bottom portion of a sixth arm, a bottom portion of a seventh arm, a bottom portion of an eighth arm, or any combination thereof may be selected to contribute to at least one of: (1) rigidity of at least one of a plurality of arms; (2) cost efficiency of a coupling device; or (3) a specific buoyancy of a coupling device, in some embodiments.

In some embodiments, a top portion and/or a bottom portion of at least one of a plurality of arms may be structurally reinforced. For example, a top portion and/or a bottom portion of at least one of a plurality of arms may have ribbing, corrugation, and/or inlays.

According to some embodiments, a plurality of arms may be configured to maximize a transfer of energy from a fluid conveyance to a coupling device. In some embodiments, at least a portion (e.g., a bottom portion) of one of a plurality of arms of a coupling device may be configured such that a first side may be impacted by a first force from a fluid conveyance and a second side may be impacted by a second force from a fluid conveyance. At least a portion (e.g., a bottom portion) of at least one of a plurality of arms of a coupling device may be configured such that a first force and a second force are about equal, in some embodiments. According to some embodiments, at least a portion (e.g., a bottom portion) of at least one of a plurality of arms may be configured such that when impacted by a first force and a second force from a fluid conveyance, the first force and the second force are unequal and the coupling device may rotate in a growth medium. In some embodiments, at least a portion (e.g., a bottom portion) of at least one of a plurality of arms of a coupling device may be configured such that when impacted by a first force and a second force from a fluid conveyance, the first force and the second force are unequal and the coupling device may rotate in a growth medium. For example, in some embodiments at least a portion (e.g., a bottom portion) of at least one of a plurality of arms may be curved, bent, folded, or notched (e.g., FIGS. 5A, 5B, 5C) such that when impacted by a first force and a second force from a fluid conveyance, the first force and the second force are unequal and the coupling device may rotate in a growth medium. According to some embodiments, at least a portion (e.g., a bottom portion) of at least one of a plurality of arms may be curved such that when impacted by a first force and a second force from a fluid conveyance, the first force and the second force are unequal and the coupling device may rotate in a growth medium.

In some embodiments, at least one of a plurality of arms may have a top portion comprised of a first material and a bottom portion comprised of a second material, where the first material and the second material may be the same material. According to some embodiments, at least one of a plurality of arms may comprise a single piece (e.g., cut, molded, forged). At least one of a plurality of arms may have a top portion comprised of a first material and a bottom portion comprised of a second material, where the first material and the second material may be different materials.

A hub, in some embodiments may comprise any suitable material, including, for example: wood, plastic, polystyrene, metal, a composite, a resin, a laminate, particle boards, plywood, ribbed aluminum, foam board, corrugated plastic board, or any combination thereof. A composition of a hub, according to some embodiments, may be selected to contribute to a specific buoyancy of a coupling device. According to some embodiments, a hub may be configured to house one or more devices (e.g., in or on a hub). A hub, in some embodiments may be hollow such that one or more devices (e.g., a monitoring system) may be housed inside the hub. In some embodiments a hollow hub may be water-proof. According to some embodiments one or more devices may be a monitoring system (e.g., a nutrient content of a growth medium) and/or a drive mechanism. A drive mechanism, in some embodiments, may be configured to move a coupling device (e.g., automatically, manually) from a first location in a bioreactor container to a second location in the bioreactor container. In some embodiments, a drive mechanism may be configured to rotate or translate a coupling device (e.g., manually, automatically).

In some embodiments, a hub may contain or support one or more solar panels and/or one or more batteries configured to provide energy to one or more devices housed in or on the hub.

A Support Band

According to some embodiments, a coupling device may comprise a support band. A support band, in some embodiments, may connect to a distal portion of one or more arms of a star. In some embodiments, a support band may be configured to provide structural rigidity to a coupling device. According to some embodiments, a support band may be configured to prevent a plurality of arms of a first coupling device from becoming entangled with a plurality of arms of a second coupling device or with a portion of a bioreactor.

According to some embodiments a support band may be a single band capable of sufficient flexibility (e.g., resilience) to connect to at least a portion of each of a second end of plurality of arms to form a coupling device. A support band may have any desired shape, size, or composition according to some embodiments. For example, a support band may have any regular or irregular geometric profile. A single support band when connected to a star may have a circular shape, or an oval shape, in some embodiments or a triangular shape, or a square shape, or a polygonal shape, or a hexagonal shape. According to some embodiments, a support band may have a first end, a second end, an inner portion, an upper side, and a lower side. In some embodiments, an inner portion of a support band may have at least one flat side. According to some embodiments, a cross section of an inner portion of a support band may be square, rectangular, triangular, hexagonal, polygonal, circular, oval or irregular. Each arm of a star may be contact a support band at or near its distal end (e.g., with reference to the star's connection point). A point of contact between a distal end of an arm and a support band may be coextensive with the size of the distal end of the arm and/or the support band. Where the point of contact is coextensive with only a portion of the distal end of the arm and/or the support band, the point of contact may be positioned at any point along either of the contacting parts. For example, as shown in FIG. 2, only the lower portion of distal end of arms 221, 222, 223, and 224 contacts support band 250.

In some embodiments, a support band may have a width, measured from an upper side to a lower side, of ≥0.5 cm, or ≥1 cm, or ≥2 cm, or ≥3 cm, or ≥4 cm, or ≥5 cm, or ≥10 cm, or ≥15 cm, or ≥20 cm, or ≥25 cm, or ≥30 cm, or ≥35 cm, or ≥40 cm, or ≥45 cm, or ≥50 cm, or ≥60 cm, or ≥70 cm, or ≥80 cm, or ≥90 cm, or ≥100 cm, or ≥110 cm, or ≥120 cm, or ≥130 cm, or ≥140 cm, or ≥150 cm, or ≥160 cm, or ≥170 cm, or ≥180 cm, or ≥190 cm, or ≥200 cm. According to some embodiments, a coupling device may be configured such that a width of a support band, measured from an upper side to a lower side, is less than a width of at least on of a plurality of arms, measured from an upper side to a lower side.

A coupling device, in some embodiments, may be configured such that a lower side of a support band is connected to at least a portion of each of a plurality of arms. A coupling device, in some embodiments, may be configured such that a lower side of a support band is substantially adjacent to a bottom portion of each of a plurality of arms. According to some embodiments, a coupling device may be configured such that a support band is connected to at least a portion of each of a plurality of arms such that the separator band does not contact a top portion of any of the plurality of arms. In some embodiments, a coupling device may be configured such that a support band is not connected to a top portion of any of a plurality of arms and is completely submerged in a growth medium, and the top portion of each of the plurality of arms extends above the growth medium.

According to some embodiments, a support band may be a plurality of bands with each of the plurality of bands connecting one of a plurality of arms to at least one other of the plurality of arms. For example, in some embodiments, a first end of a first support band may connect to a second end of a first arm; a second end of the first support band may connect to a second end of a second arm; a first end of a second support band may connect to the second end of the second arm; a second end of the second support band may connect to the second end of a third arm; a first end of a third support band may connect to the second end of the third arm;

and a second end of the third support band may connect to the second end of the first arm. A support band, in some embodiments, may be a plurality of bands such that a first end of a first support band may connect to a second end of a first arm; a second end of the first support band may connect to a second end of a second arm; a first end of a second support band may connect to the second end of the second arm; a second end of the second support band may connect to the second end of a third arm; a first end of a third support band may connect to the second end of the third arm; a second end of the third support band may connect to a second end of a fourth arm; a first end of a fourth support band may connect to the second end of the fourth arm; and a second end of the fourth support band may connect to the second end of the first arm. In some embodiments, a support band may be a plurality of bands with each of the plurality of bands connected to one another and/or connected to one or more of a plurality of arms.

In some embodiments, a support band may be a plurality of bands with each of the plurality of bands connecting one of a plurality of arms to at least two other of the plurality of arms. For example, in some embodiments, a first end of a first support band may connect to a second end of a first arm, and a second end of the first support band may connect to a second end of a third arm, such that an inner portion of the first support band connects to a second end of a second arm.

A composition of a support band, according to some embodiments, may be selected to contribute to a specific buoyancy of a coupling device. According to some embodiments a support band may comprise any suitable material, including for example: wood, plastic, polystyrene, metal, a composite, a resin, a laminate, particle board, plywood, mesh, chicken wire, ribbed aluminum, foam board, corrugated plastic board, woven fabric, wire, rope, string, or any combination thereof.

Buoyancy

According to some embodiments, a coupling device may be configured to be up to completely submerged in a growth medium. If completely submerged, a coupling device may have sufficient buoyancy relative to the media in which it is used to be positioned at (e.g., immediately below) the media's surface. In some embodiments, >0.05 cm, or >0.1 cm, or >0.2 cm, or >0.3 cm, or >0.4 cm, or >0.5 cm, or >0.6 cm, or >0.7 cm, or >0.8 cm, or >0.9 cm, or >1 cm, or ≥2 cm, or ≥3 cm, or ≥4 cm, or ≥5 cm, or ≥10 cm, or ≥15 cm, or ≥20 cm, or ≥25 cm, or ≥30 cm, or ≥35 cm, or ≥40 cm, or ≥45 cm, or ≥50 cm, or ≥60 cm, or ≥70 cm, or ≥80 cm, or ≥90 cm, or ≥100 cm, or ≥110 cm, or ≥120 cm, or ≥130 cm, or ≥140 cm, or ≥150 cm, or ≥160 cm, or ≥170 cm, or ≥180 cm, or ≥190 cm, or ≥200 cm of a height of at least one of a plurality of arms may be submerged when a coupling device is placed in a growth medium. According to some embodiments ≥1%, or ≥2%, or ≥3%, or ≥4%, or ≥5%, or ≥6%, or ≥7%, or ≥8%, or ≥9%, or ≥10%, or ≥20%, or ≥30%, or ≥40%, or ≥50%, or ≥60%, or ≥70%, or ≥80%, or ≥90%, or ≥95%, or ≥98% of a height of at least one of a plurality of arms may be submerged when a coupling device is placed in a growth medium. A support band may be completely submerged, in some embodiments.

A buoyancy of a coupling device may be adjusted according to some embodiments. For example, at least one weight or flotation device may be fitted to a coupling device. In some embodiments, at least one weight or flotation device may be fixedly fitted to and/or into a coupling device. According to some embodiments, at least one weight or flotation device may be removably fitted to a coupling device such that a buoyancy of the coupling device is adjustable in response to changing conditions. At least one weight or flotation device may be fitted (e.g., removably) to at least one of: (1) at least one of a plurality of arms; (2) a hub; and (3) a support band. According to some embodiments, at least one weight or flotation device may be inserted into a hub (e.g., a hollow hub).

Assembly

According to some embodiments, a coupling device may be pre-manufactured as individual components for efficient delivery and assembly. For example, a star of a coupling device may be a first blade and a second blade joined at a connection point (e.g., FIG. 3B, FIG. 3D). In some embodiments, a first blade and a second blade may be manufactured for ease of shipping and/or cost effectiveness (e.g., flat pack, stackable, molded plastic, extruded plastic).

Disruptor

In some embodiments, a coupling device may further comprise a disruptor configured to disrupt or dislodge a particulate matter (e.g., debris, dead microcrop tissue) from at least one surface (e.g., floor, peripheral wall) of a bioreactor container. A disruptor, according to some embodiments) may be configured to transfer a particulate matter (e.g., debris, dead microcrop tissue) from at least one surface of a bioreactor container into suspension or partial suspension such that at least a portion of the particulate matter may be removed from the bioreactor container. In some embodiments at least a portion of a suspended or partially suspended particulate matter may be removed from a bioreactor system by a filter mechanism (e.g., inline filter of fluid conveyance mechanism).

According to some embodiments a disruptor may be fixedly or removably attached to a connection point (e.g., a hub), at least one support band, or at least one arm of a coupling device. In some embodiments, a disruptor may be suspended from (e.g., flexibly, rigidly) a connection point (e.g., FIG. 9A), at least one arm, at least one support band, or any combination thereof. A disruptor, in some embodiments, may be fixedly or removably connected to a lower side or an exterior side (i.e., a side facing towards a peripheral wall and away from a hub) of a support band (e.g., FIG. 9B). In some embodiments a disruptor may be fixedly or removably connected to a lower side of at least one arm (not shown).

In some embodiments a disruptor may be configured to scrape at least one surface of a bioreactor container thereby resulting in suspension of a particulate matter. A disruptor, in some embodiments, may be configured to generate a current of a growth medium thereby suspending a particulate matter. In some embodiments, a disruption device may not contact a surface of a bioreactor container (e.g., floor, peripheral wall).

In some embodiments a disruptor may comprise one or more bristles. A disruptor, according to some embodiments, may comprise plastic, metal, rubber, woven fabric, wire, rope, or string. A composition of a disruptor may be selected to prevent wear of one or more surfaces of a bioreactor container (e.g., floor, peripheral wall). In some embodiments a coupling device comprising a disruptor may disrupt or dislodge a particulate matter from at least one surface of a bioreactor container as a result of a rotation of the coupling device (e.g., wind, motor function, a drive mechanism).

Shade Netting

A coupling device, in some embodiments, may further comprise a shade netting suspended from a top surface of the coupling device and moveably, removably or fixedly attached to at least one of a plurality of arms or a hub. According to some embodiments, a shade netting may be suspended above a coupling device and moveably, removably or fixedly attached to an extension (e.g., pole) that is moveably, removably or fixedly attached to at least one of a plurality of arms or a hub. In some embodiments, a shade netting may be suspended such that the shade netting is parallel to a top surface of a coupling device. In some embodiments a shade netting may cover or cast shade on at least 10%, or 20%, or 30%, or 40%, or 50%, or 60%, or 70%, or 80%, or 90%, or 100% of a top surface of a coupling device. According to some embodiments, a shade netting may be suspended such that the shade netting extends beyond a second end of at least one of a plurality of arms of a coupling device from which the shade netting suspended. Shade netting may comprise a fabric or a plastic mesh, in some embodiments.

Monitoring System

In some embodiments, a bioreactor system may comprise a monitoring system. A monitoring system may be configured to display and/or provide one or more user alerts regarding bioreactor condition(s) (e.g., nutrient concentrations, pH, dissolved oxygen levels, growth medium levels, microcrop distribution, flow rate, temperature) and/or adjust operating conditions (e.g., growth medium flow rate and/or timing and/or quantity of nutrient addition; "feeder" microcrop addition, oxygen or carbon dioxide addition), in some embodiments. Adjustments may be made continuously, semi-continuously, periodically, intermittently, as needed, at set or variable times, or any other interval. In some embodiments, adjustments may be selected to optimize growth rates and/or yield of the aquatic species. For example, a microcrop species may be grown in large-scale, open bioreactors with monitoring systems configured to adjust the introduction of materials (e.g., fresh or recycled water, fresh or recycled growth media) based on, for example, exposure to light, which may thereby regulate nutrient consumption rates.

A bioreactor system, in some embodiments, may monitor and adjust a thickness and distribution of a microcrop mat. For example, when a microcrop reaches a specified thickness or distribution a bioreactor system may initiate harvest procedures.

FIGS. 1A and 1B illustrate an aerial view of a bioreactor system configured for cultivating a microcrop (e.g., aquatic plant species, *Lemna*, algal species), according to one embodiment of the disclosure. As shown in FIGS. 1A and 1B, a bioreactor system 100 may comprise a bioreactor container 102, a growth medium (not shown), a fluid conveyance 104, a monitoring system 106, and at least one coupling device 110.

According to some embodiments, a bioreactor container 102 may be a raceway, as shown in FIG. 1A, or a serpentine raceway, as shown in FIG. 1B. In some embodiments, a bioreactor container may have one or more channels 105. According to some embodiments, a bioreactor system 102 may be configured such that a growth medium and/or a microcrop biomass may be conveyed (e.g., propelled) in one or more bioreactor containers such that the microcrop biomass travels in a continuous loop. As shown in FIGS. 1A and 1B, in some embodiments, a bioreactor system 100 may be open along a top surface (e.g., in a horizontal plane relative to the sky) of a bioreactor container 102.

A bioreactor system may contain a growth medium (not shown). In some embodiments a growth medium may comprise water and/or a nutrient composition. A growth medium (e.g., water) may be provided in and/or added to a bioreactor container 102 and may be maintained at a desired set-point level (e.g., specific volume, specific depth), according to some embodiments. A bioreactor system may be configured to insert additional nutrients (e.g., nitrogen, phosphorus, potassium) or gases (e.g., oxygen; carbon dioxide) into a growth medium (e.g., water) at specified time indicators or in response to sensor readings.

As shown in FIGS. 1A and 1B, a bioreactor system 100 may include one or more fluid conveyances 104. In some embodiments a fluid conveyance 104 may be at least one of a plurality of underwater jets, a bubbler, an underwater mixer, a paddle wheel, a recirculation system, and an axial/centrifugal mixer. A fluid conveyance 104, in some embodiments, may be an underwater propulsion mechanism (e.g., underwater jets, a bubbler, an axial/centrifugal mixers).

In some embodiments, a bioreactor system 100 may be configured to adjust the flow rate of a growth medium (e.g., to redistribute nutrient concentrations or microcrop growth patterns). According to some embodiments, a fluid conveyance 104 may be configured to convey (e.g., propel) a growth medium through a bioreactor container 102 in a continuous loop at a velocity of about 0.01 m/s, or about 0.05 m/s, or about 0.1 m/s, or about 0.15 m/s, or about 0.2 m/s, or about 0.25 m/s, or about 0.3 m/s, or about 0.35 m/s, or about 0.4 m/s, or about 0.45 m/s, or about 0.5 m/s, or about 0.55 m/s, or about 0.6 m/s, or about 0.65 m/s, or about 0.7 m/s, or about 0.75 m/s, or about 0.8 m/s, or about 0.85 m/s, or about 0.9 m/s, or about 0.95 m/s, or about 1.0 m/s. According to some embodiments, a fluid conveyance 104 may release a propulsion stream 103 that may function to convey (e.g., propel and/or impel) a growth medium and/or a microcrop floating on a surface of the growth medium.

In some embodiments, a fluid conveyance may be situated at any point within a bioreactor container. A fluid conveyance, in some embodiments, may be situated on a bottom of a bioreactor container. As shown in FIG. 1B, in some embodiments, a fluid conveyance 104 may be situated on one or more sides or peripheral walls of a bioreactor container. In some embodiments, a fluid conveyance may extend across a channel in a bioreactor system, as shown in FIGS. 1A and 1B. As shown in FIG. 1B, in some embodiments, a bioreactor system may have a plurality of fluid conveyance mechanisms 104 with the fluid conveyance mechanisms situated in multiple locations within the bioreactor system, including on one or more sides or peripheral walls of a bioreactor container, on a bottom of the bioreactor container, and/or extending across a channel.

As shown in FIGS. 1A and 1B, a bioreactor system may comprise a monitoring system 106. A monitoring system may be configured to display and/or provide one or more user alerts regarding bioreactor condition(s) (e.g., nutrient concentrations, pH, dissolved oxygen levels, growth medium levels, microcrop distribution, flow rate, temperature) and/or adjust operating conditions (e.g., growth medium flow rate and/or timing and/or quantity of nutrient addition; "feeder" microcrop addition, oxygen or carbon dioxide addition), in some embodiments. Adjustments may be made continuously, semi-continuously, periodically, intermittently, as needed, at set or variable times, or any other interval. In some embodiments, adjustments may be selected to optimize growth rates and/or yield of the aquatic species.

A bioreactor system 100, may further comprise at least one coupling device 110. As shown in FIGS. 1A and 1B, a bioreactor system 100 may comprise a plurality of coupling devices 110. Each of a plurality of coupling devices 110 in a bioreactor system may be the same, as shown in FIGS. 1A and 1B. In some embodiments, at least one member of a plurality of coupling devices 110 may be different than the other members of the plurality of coupling devices.

According to some embodiments, a coupling device 110 may comprise a plurality of arms 120 and a support band 150. A coupling device 110 may be configured to transfer energy from a fluid conveyance 104 to a microcrop floating on a surface of a growth medium, according to some embodiments. As shown in FIGS. 1A and 1B, transferring an energy from a fluid conveyance 104 to a coupling device 110 may initiate movement of the coupling device. Movement of a coupling device 110, may include rotation 115 and/or translation 114 and may redistribute a portion of a growth medium and/or a portion of a microcrop. According to some embodiments, movement may be at least one of counterclockwise or clockwise rotation 115 of a coupling device. In some embodiments, movement of a coupling device 110 may fluctuate between a counterclockwise rotation and a clockwise rotation. In some embodiments, each of a plurality of coupling devices may move independently, such that at a given point in time at least one of the plurality of coupling devices may rotate in a direction that is different than at least one other of the plurality of coupling devices. Movement, in some embodiments, may be translation 114 of a coupling device from a first point to a second point.

FIG. 2 illustrates a perspective view of a coupling device according to one embodiment of the disclosure. As shown in FIG. 2, a coupling device 200 may comprise a star 241 and a support band 250. A star may be formed by joining a plurality of arms at a connection point (e.g., hub), according to some embodiments. As shown in FIG. 2, a star 241 may comprise a first arm 221, a second arm 223, a third arm 222, a fourth arm 224 joined at a connection point 240. A star 241 may comprise any number of arms (e.g., three arms, four arms, five arms, six arms, seven arms, eight arms). A plurality of arms may be connected at a connection point 240 to form a star 241, in some embodiments. As shown in FIG. 2, a support band 250 may be connected to a star 241 by connecting to at least a portion of each of a plurality of arms.

Figure 3C:
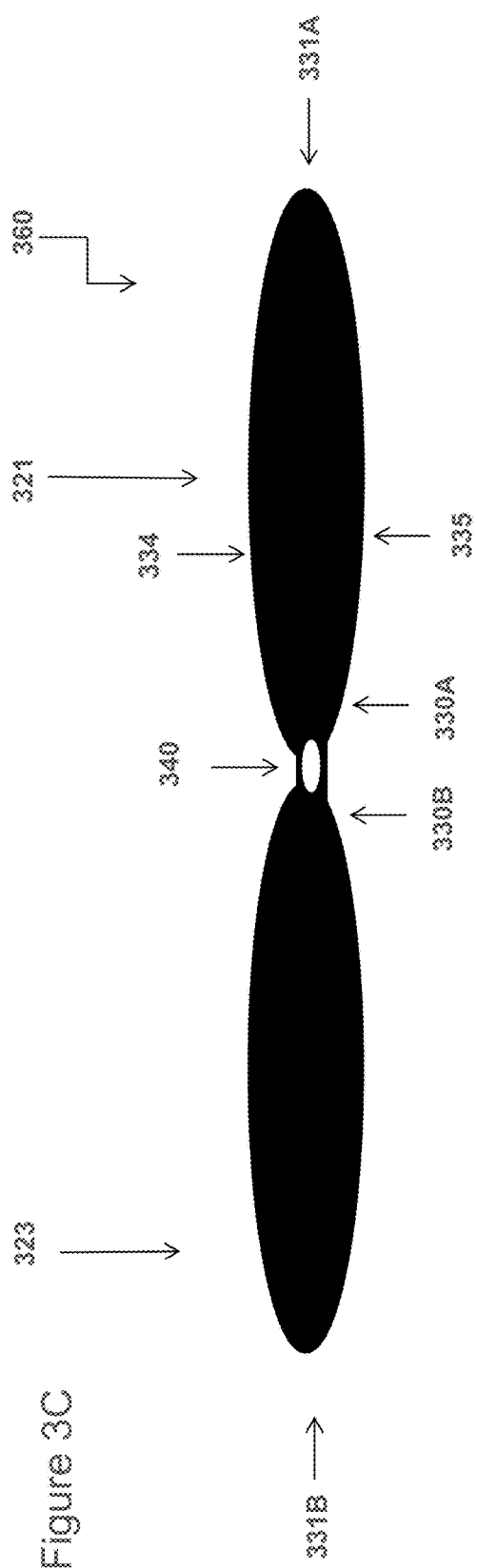
FIG. 3C illustrates a perspective view of a blade, according to one embodiment of the disclosure.
Figure 3D:
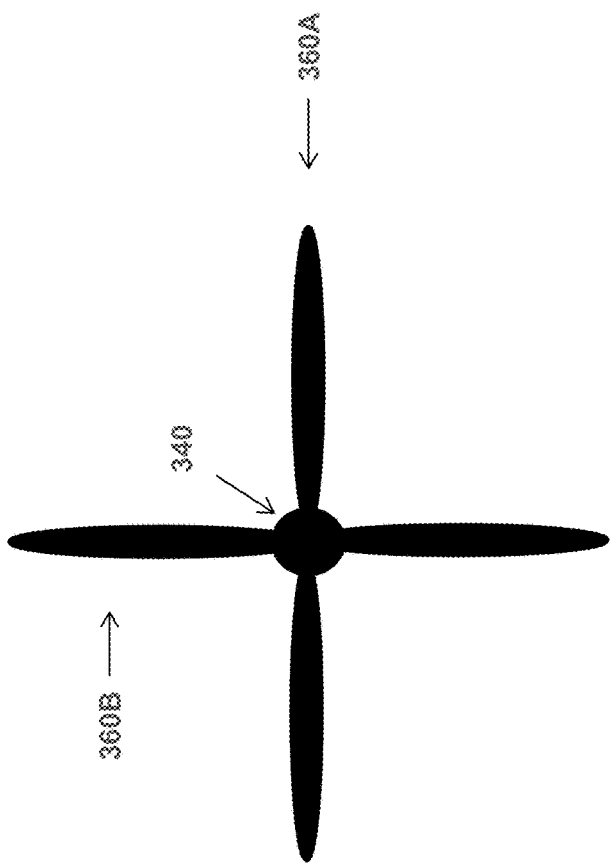
FIG. 3D illustrates an aerial view of a star comprising a first blade and a second blade, according to one embodiment of the disclosure.

FIGS. 3A and 3C illustrate a perspective view of a blade, according to some embodiments of the disclosure. FIG. 3B illustrates a perspective view of a method of assembling a star comprising a first blade and a second blade, according to one embodiment of the disclosure. FIG. 3D illustrates an aerial view of a star comprising a first blade and a second blade, according to one embodiment of the disclosure.

As shown in FIGS. 3A and 3C, a blade 360 may be comprise a first arm 321 joined to a second arm 323, and further comprise a connection point 340. Each of a first arm and a second arm forming a blade may have a first end 330A/330B, a second end 331A/331B, a first side, a second side, an upper side 334, and a lower side 335, with a first end of the first arm and a first end of the second arm being connected. In some embodiments, as shown in FIG. 3A, an upper side 334 and a lower side 335 of a first arm and a second arm comprising a blade may be substantially straight and may be substantially parallel to an upper surface of a growth medium. As shown in FIG. 3C, in some embodiments, an upper side 334 and a lower side 335 of a first arm and a second arm comprising a blade may be curved.

In some embodiments, a connection point may comprise a point in space where a first blade may be joined to a second blade and/or a third blade (e.g., slot, melt fusion, adhesion, bridle, finger, dado, dovetail, dowel, screw, bolt, rivet joints). A blade 360 may further comprise a slot (as shown in FIG. 3A) or hole (as shown in FIG. 3C) at a connection point 340 to facilitate joinder to a second blade and/or a third blade.

As shown in FIG. 3B and FIG. 3D, a star 341 of a coupling device may be a first blade 360A and a second blade 360B joined at a connection point 340. According to some embodiments, a coupling device may be pre-manufactured as individual components for efficient delivery and assembly. In some embodiments, a first blade and a second blade may be manufactured for ease of shipping and/or cost effectiveness (e.g., flat pack, stackable, molded plastic, extruded plastic). As shown in FIG. 3B, a star 341 may be assembled by connecting a first blade 360A and a second blade 360B at a connection point 340. Such joinder may occur by connecting a slot 340A of a first blade 360A with a slot 340B of a second blade 360B, as shown in FIG. 3B, where the slots are located at the connection point. As shown in FIGS. 3C and 3D, a first blade 360A and a second blade 360B may comprise a hole at their respective connection point 340, and may be connected by alignment of the respective connection points and securing a connection device (e.g., bolt, screw, rivet) through the hole to form a star 341.

Figure 4A:
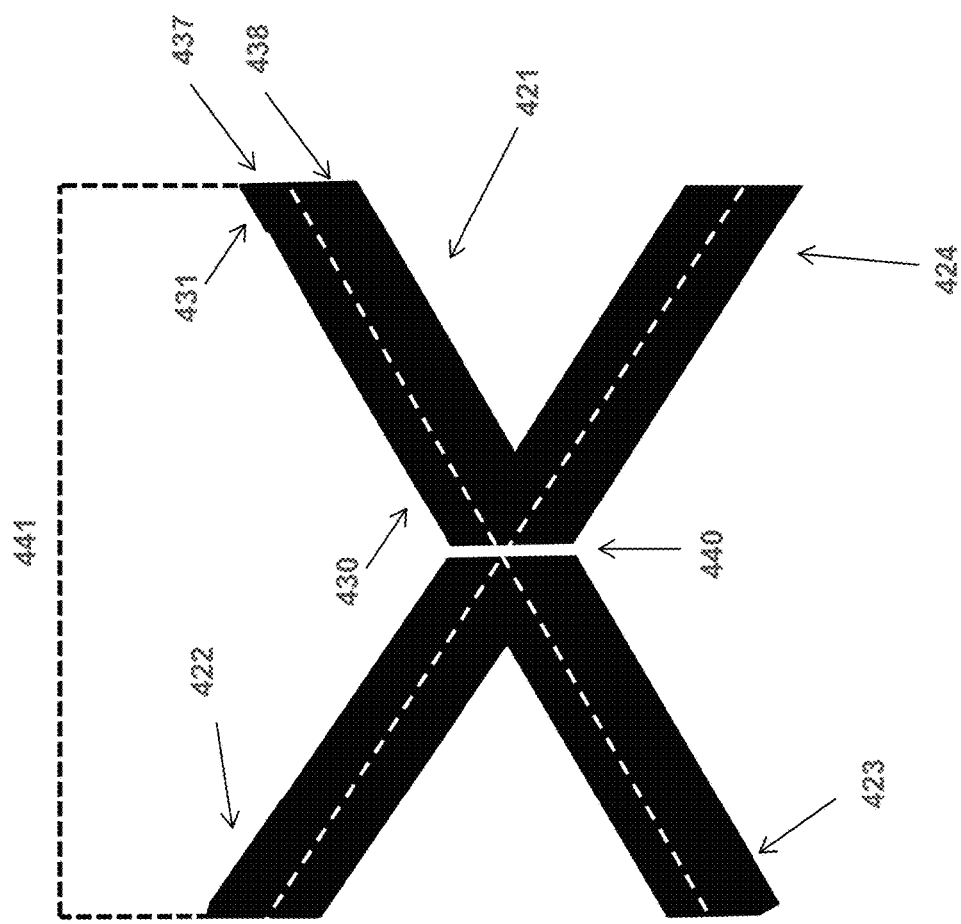
FIG. 4A illustrates a perspective view of a star, according to one embodiment of the disclosure.

FIGS. 4A and 4B illustrate perspective views of a star, according to example embodiments of the disclosure. In some embodiments, a plurality of arms may be connected at a connection point 440 to form a star 441. Each of the plurality of arms may comprise a first end 430 and a second end 431. As shown in FIGS. 4A and 4B, a star 441 may have a first end 430 of a first arm 421, a first end 430 of a second arm 422, a first end 430 of a third arm 423, and a first end 430 of a fourth arm 424 connected to and extending from a connection point 440. According to some embodiments, and as shown in FIG. 4A, a connection point 440 may be a common point in space where a first end of a plurality of arms are fixedly attached to one another such that a second end 431 of each of the plurality of arms extend outward away from the connection point 440. A second end 431 of each of a plurality of arms, in some embodiments, may extend outward from a connection point such that the plurality of arms are in a single plane and parallel to an upper surface of a growth medium.

As shown in FIG. 4A, a connection point 440 may be a point in space. As shown in FIG. 4B, a connection point 440 may be a hub. In some embodiments, a hub may be cylindrical (e.g., FIG. 4B), ring shaped, square, polygonal, spherical, or any other suitable shape. A hub may include indentations, slots, or threaded holes in which a first end of a plurality of arms may be inserted.

According to some embodiments, a star may be configured with a plurality of arms equally spaced around a connection point (e.g., point in space, vertex, hub). For example, as shown in FIG. 4A and FIG. 4B, a star 441 may be configured with four arms spaced 90° apart. In some embodiments, a star may be configured with three arms at 120° apart; or five arms at 72° apart; or six arms at 60° apart; or seven arms at 51.4° apart; or eight arms at 45° apart. A star, in some embodiments, may be configured with a plurality of arms unequally spaced around a connection point. For example, a star may be configured with a first arm spaced 180° from a second arm and a third arm spaced 90° from the second arm.

A star, in some embodiments, may be configured such that when the star is immersed in a growth medium top portion 437 of a plurality of arms may be above a surface of the growth medium and a bottom portion 438 may be submerged. According to some embodiments, a star may be configured such that when immersed in a growth medium a second end 431 of a plurality of arms may be oriented perpendicular to an upper surface (e.g., in a horizontal plane relative to the sky) of the growth medium.

A hub, in some embodiments may comprise any suitable material, including, for example: wood, plastic, polystyrene, metal, a composite, a resin, a laminate, particle boards, plywood, ribbed aluminum, foam board, corrugated plastic board, or any combination thereof. A composition of a hub, according to some embodiments, may be selected to contribute to a specific buoyancy of a coupling device. According to some embodiments, a hub may be configured to house one or more devices (e.g., in or on a hub). A hub, in some embodiments may be hollow such that one or more devices (e.g., a monitoring system) may be housed inside the hub. In some embodiments a hollow hub may be waterproof. According to some embodiments one or more devices may be a monitoring system (e.g., a nutrient content of a growth medium) and/or a drive mechanism. A drive mechanism, in some embodiments, may be configured to move a coupling device (e.g., automatically, manually) from a first location in a bioreactor container to a second location in the bioreactor container. In some embodiments, a drive mechanism may be configured to rotate a coupling device (e.g., manually, automatically).

In some embodiments, a hub may contain or support one or more external solar panels and/or one or more batteries configured to provide energy to one or more devices housed in or on the hub.

Figure 5B:
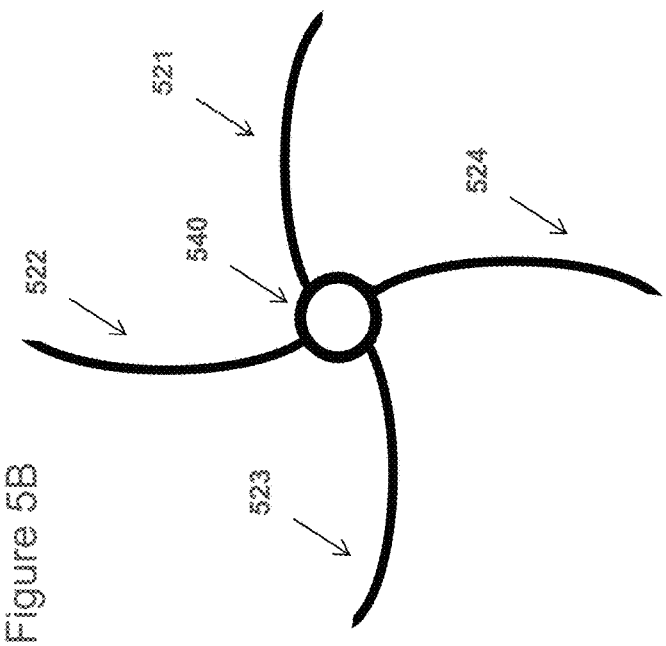
FIG. 5B illustrates an aerial view of a star, according to one embodiment of the disclosure.
Figure 5A:
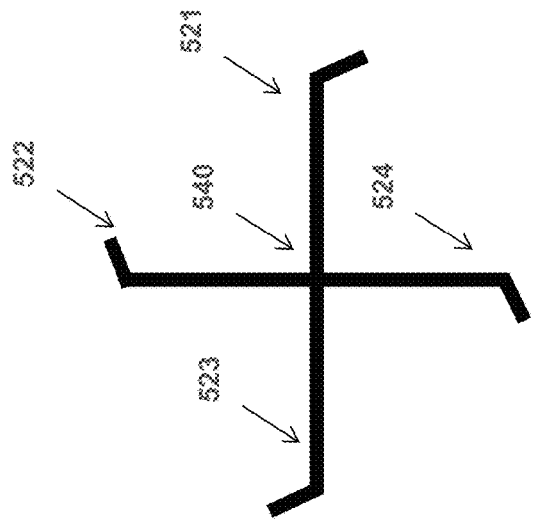
FIG. 5A illustrates an aerial view of a star, according to one embodiment of the disclosure.

FIG. 5A illustrates an aerial view of a star according to some embodiments of the disclosure. As shown in FIG. 5A, a star may comprise a first arm 521, a second arm 522, a third arm 523, and a fourth arm 524 joined at a connection point 540. At least one of a first arm 522, a second arm 522, a third arm 523, and a fourth arm 524 may be bent, as shown in FIG. 5A, such that when impacted by a first force and a second force from a fluid conveyance, the first force and the second force are unequal and a star may rotate in a growth medium.

FIG. 5B illustrates an aerial view of a star according to some embodiments of the disclosure. As shown in FIG. 5B, a star may comprise a first arm 521, a second arm 522, a third arm 523, and a fourth arm 524 joined at a connection point 540. In some embodiments, as shown in FIG. 5B, a connection point 540 may be a hub. At least one of a first arm 522, a second arm 522, a third arm 523, and a fourth arm 524 may be curved, as shown in FIG. 5B, such that when impacted by a first force and a second force from a fluid conveyance, the first force and the second force are unequal and a star may rotate in a growth medium.

Figure 5C:
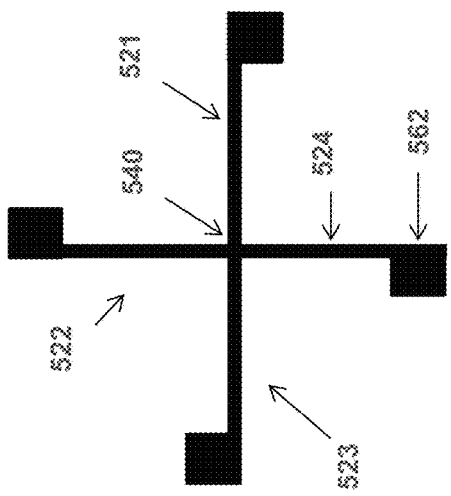
FIG. 5C illustrates an aerial view of a star, according to one embodiment of the disclosure.

FIG. 5C illustrates an aerial view of a star according to some embodiments of the disclosure. A star may comprise a first arm 521, a second arm 522, a third arm 523, and a fourth arm 524 joined at a connection point 540, according to some embodiments. A star may further comprise, one or more weight and/or flotation devices. As shown in FIG. 5C, in some embodiments a flotation device 562 may be fitted to a first arm 521, a second arm 522, a third arm 523, and a fourth arm 524. Fitting a flotation device 562 or weight to a star may make it such that when impacted by a first force and a second force from a fluid conveyance, the first force and the second force are unequal and a star may rotate in a growth medium. Fitting a flotation device 562 or weight to a star may alter a buoyancy of a coupling device may be adjusted according to some embodiments. In some embodiments at least one weight or flotation device may be fitted (e.g., moveably, removably, fixedly) to at least one of: (1) at least one of a plurality of arms; (2) a hub; and (3) a support band.

Figure 6C:
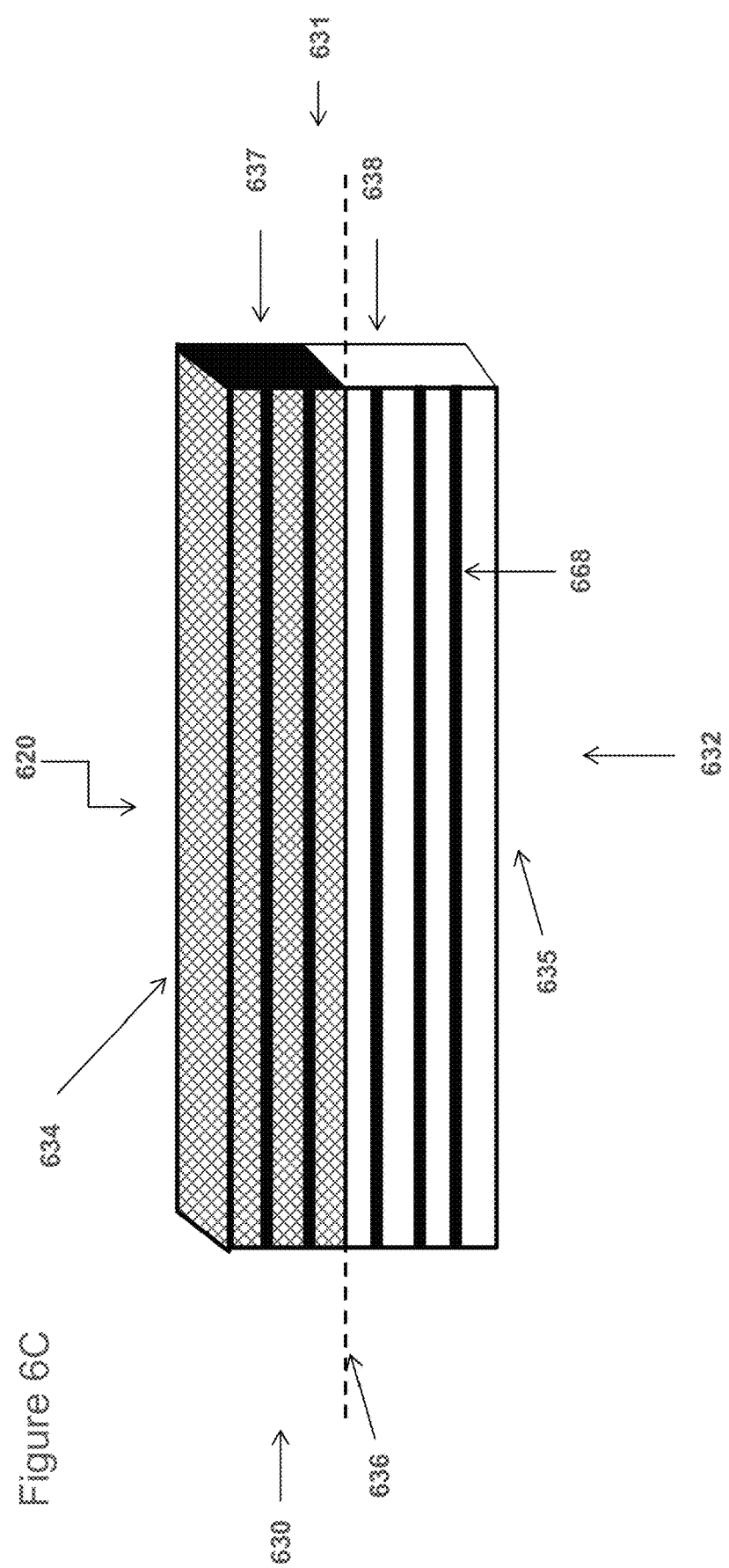
FIG. 6C illustrates a perspective view of an arm, according to one embodiment of the disclosure.

FIGS. 6A, 6B, and 6C illustrate a perspective view of an arm, according to one embodiment of the disclosure. An arm 620 may have a first end 630, a second end 631, a first side 632, a second side, an upper side 634, and a lower side 635.

According to some embodiments, an arm 620 of a coupling device may be partially submerged in a growth medium within a bioreactor container (e.g., 102) along an axis 636 (e.g., parallel to a surface of the growth medium) such that a top portion 637 of the arm is above the axis 636 and a bottom portion 638 of the arm is below axis 636 (e.g., submerged in the growth medium). In some embodiments, a top portion 637 of an arm 620 may be configured to separate or re-distribute a biomass of a microcrop. A bottom portion 638 of an arm 620 may be configured to transfer an energy from a fluid conveyance to a coupling device, in some embodiments.

In some embodiments, a top portion 637 of an arm 620 may comprise any suitable material, including for example: wood, plastic, polystyrene, metal, a composite, a resin, a laminate, particle board, plywood, mesh, chicken wire, ribbed aluminum, foam board, corrugated plastic board, or any combination thereof. A top portion of a plurality of arms may be configured such that a growth medium and/or a microcrop may flow through portions of the top portion (e.g., FIG. 6B, 6C). According to some embodiments, a top portion of a plurality of arms may be configured to separate or re-distribute a biomass of a microcrop. For example, as shown in FIG. 6B, a top portion of a plurality of arms may comprise a plurality of slots 664 such that a growth medium and/or portions of a biomass may flow through slots 664. As shown in FIG. 6C, a top portion of a plurality of arms may comprise a mesh such that a growth medium and/or portions of a biomass may flow through portions of the top portion 637.

At least one of a bottom portion of a plurality of arms may comprise any suitable material, including, for example: wood, plastic, polystyrene, metal, a composite, a resin, a laminate, particle boards, plywood, ribbed aluminum, foam board, corrugated plastic board, or any combination thereof.

In some embodiments, a top portion and/or a bottom portion of at least one of a plurality of arms may be structurally reinforced. As shown in FIG. 6C, a top portion and/or a bottom portion of at least one of a plurality of arms may have ribbing 668.

As shown in FIG. 6A, in some embodiments, at least one of a plurality of arms may have a top portion comprised of a first material and a bottom portion comprised of a second material, where the first material and the second material may be the same material. According to some embodiments, at least one of a plurality of arms may comprise a single piece (e.g., cut, molded, forged). As shown in FIGS. 6B and 6C, in some embodiments at least one of a plurality of arms may have a top portion comprised of a first material and a bottom portion comprised of a second material, where the first material and the second material may be different materials.

Figure 7A:
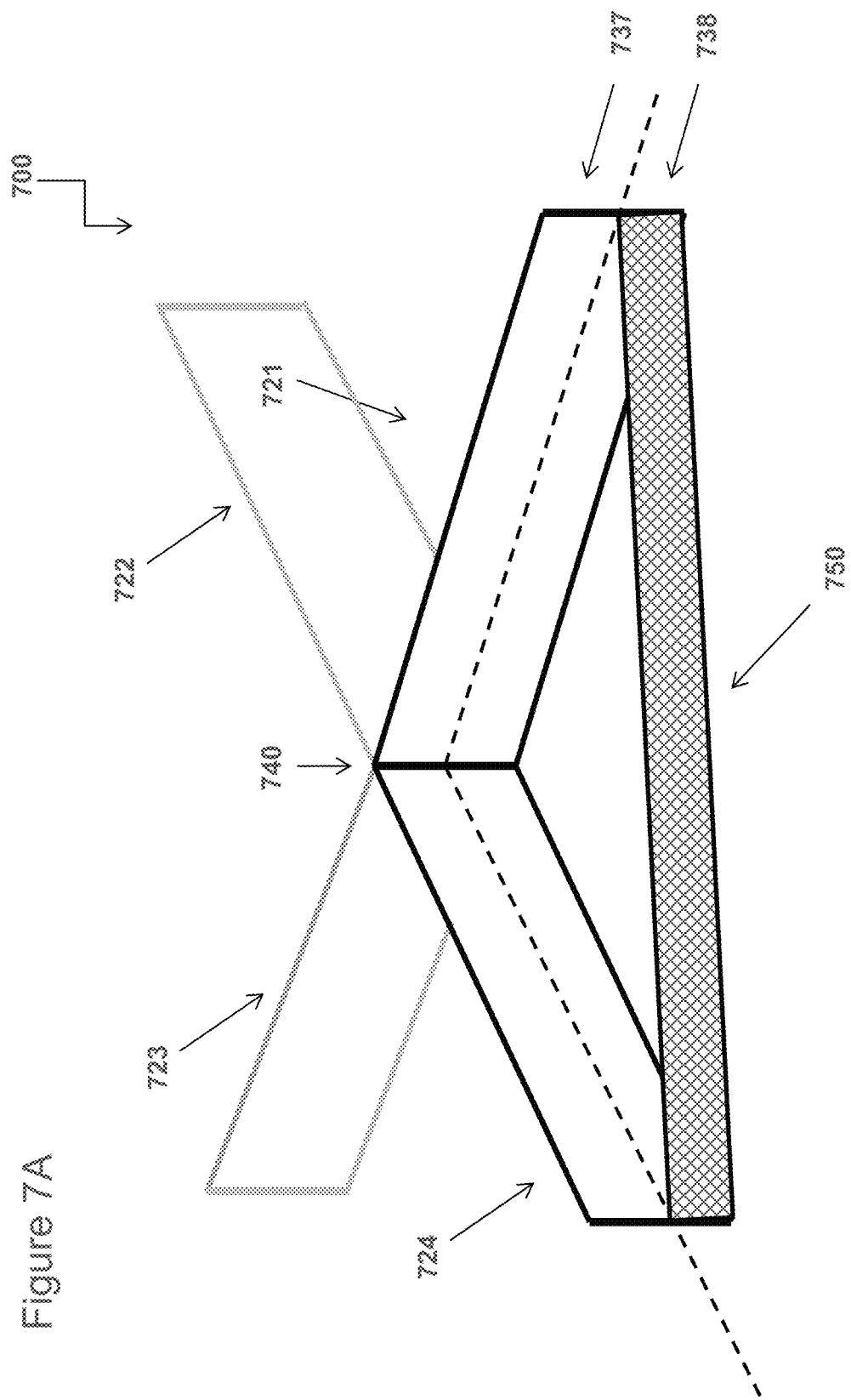
FIG. 7A illustrates a perspective view of a coupling device, according to one embodiment of the disclosure.

FIGS. 7A and 7B illustrates a perspective view of a coupling device, according to one embodiment of the disclosure. According to some embodiments, a coupling device may comprise a plurality of arms joined at a connection point and a support band. In some embodiments a coupling device may comprise a plurality or arms joined at a connection point.

As shown in FIGS. 7A and 7B, a coupling device 700 may comprise a first arm 721, a second arm 722 (shown in shadow), a third arm 723 (shown in shadow), a fourth arm 724 and a portion of a support band 750. A coupling device may comprise any number of arms (e.g., three arms, four arms, five arms, six arms, seven arms, eight arms). Each of the plurality of arms may comprise a first end 730 and a second end 731, a top portion 737, and a bottom portion 738, in some embodiments. A first end 730 of each of plurality of arms may be connected at a connection point 740 to form a star, in some embodiments.

A support band 750 may be connected to at least a portion of a second end 731 of each of a plurality of arms to form a coupling device 700. As shown in FIGS. 7A and 7B, a support band 750 may be connected to a bottom portion 738 of each of a plurality of arms.

A composition of a support band, according to some embodiments, may be selected to contribute to a specific buoyancy of a coupling device. According to some embodiments a support band may comprise any suitable material, including for example: wood, plastic, polystyrene, metal, a composite, a resin, a laminate, particle board, plywood, mesh, chicken wire, ribbed aluminum, foam board, corrugated plastic board, woven fabric, wire, rope, string, or any combination thereof. As shown in FIG. 7A, a support band 750 may be comprised of a mesh material such that portions of a growth medium may flow through portions of the support band. In some embodiments, as shown in FIG. 7A, a support band 750 may comprise a strip of material (e.g., wood, plastic, woven fabric, mesh), having a width less than a height of an arm to which the support band is connected. As shown in FIG. 7B, a support band may be wire or string.

FIGS. 8A, 8B, 8C, 8D, 8E, and 8F illustrate an aerial view of a coupling device, according to specific embodiments of the disclosure. According to some embodiments, a coupling device 800 may comprise a plurality of arms 820 joined at a connection point to form a star and a support band 850.

Figure 8A:
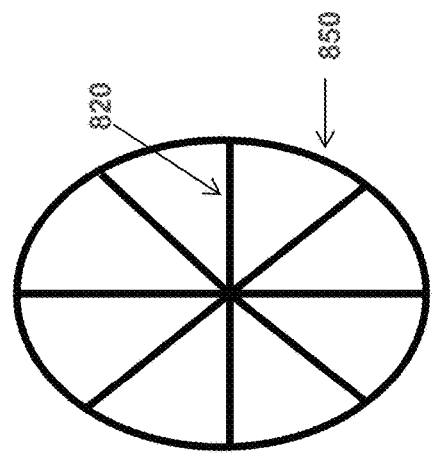
FIG. 8A illustrates an aerial view of a coupling device, according to a specific embodiment of the disclosure.
Figure 8B:
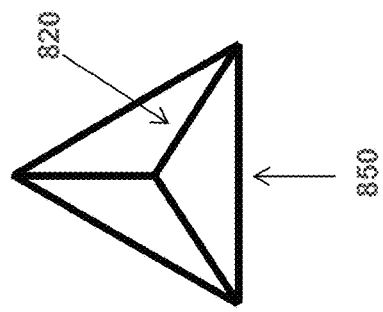
FIG. 8B illustrates an aerial view of a coupling device, according to a specific embodiment of the disclosure.
Figure 8C:
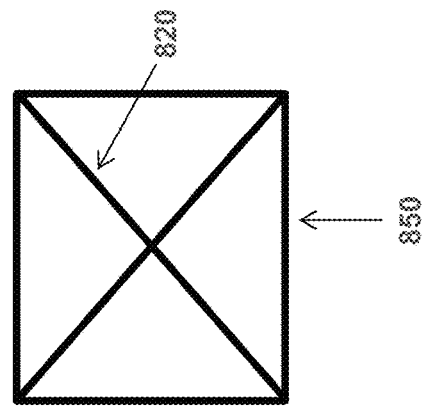
FIG. 8C illustrates an aerial view of a coupling device, according to a specific embodiment of the disclosure.
Figure 8D:
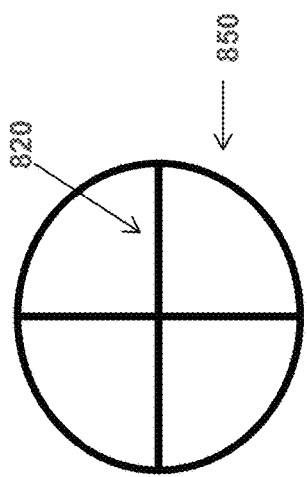
FIG. 8D illustrates an aerial view of a coupling device, according to a specific embodiment of the disclosure.
Figure 8E:
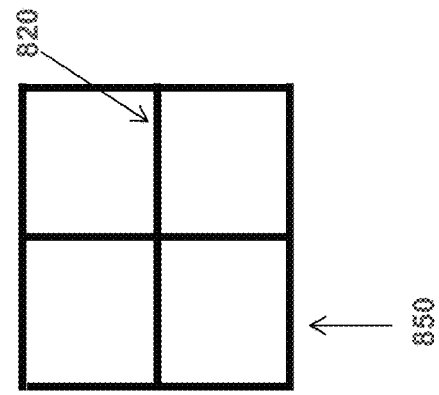
FIG. 8E illustrates an aerial view of a coupling device, according to a specific embodiment of the disclosure.
Figure 8F:
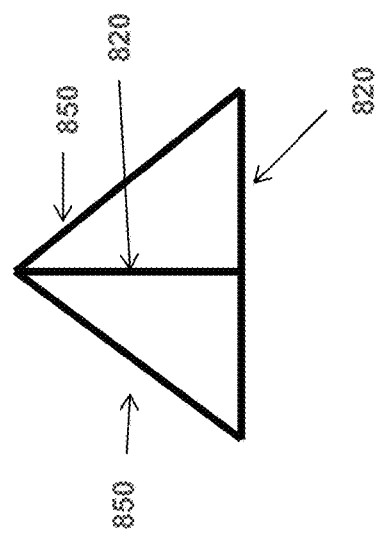
FIG. 8F illustrates an aerial view of a coupling device, according to a specific embodiment of the disclosure.

According to some embodiments, a star may be configured with a plurality of arms equally spaced around a connection point (e.g., point in space, hub). For example, as shown in FIG. 8A and FIG. 8E, a star may be configured with four arms spaced 90° apart. As shown in 8B, a star may be configured with three arms at 120° apart. A star may be configured with five arms at 72° apart, in some embodiments. According to some embodiments, a star may be configured with six arms at 60° apart. In some embodiments, a star may be configured with seven arms at 51.4° apart. A star may be configured with eight arms at 45° apart, in some embodiments, as shown in FIG. 8C. A star, in some embodiments, may be configured with a plurality of arms unequally spaced around a connection point. For example, a star may be configured with a first arm spaced 180° from a second arm and a third arm spaced 90° from the second arm, as shown in FIG. 8D.

A support band, in some embodiments, may connect to a star by connecting to at least a portion of each of a second end of a plurality of arms to form a coupling device. In some embodiments, a support band may be configured to provide structural rigidity and/or resilience to a coupling device. According to some embodiments, a support band may be configured to prevent a plurality of arms of a first coupling device from becoming entangled with a plurality of arms of a second coupling device.

According to some embodiments a support band may be a single band capable of sufficient flexibility to connect to at least a portion of each of a second end of plurality of arms to form a coupling device. A single support band when connected to a star may have a circular shape, as shown in FIG. 8A. In some embodiments, as shown in FIGS. 8B and 8D, a support band when connected to a star may have a triangular shape. As shown in FIG. 8C, a support band may have a oval shape when connected to a star.

Figure 9B:
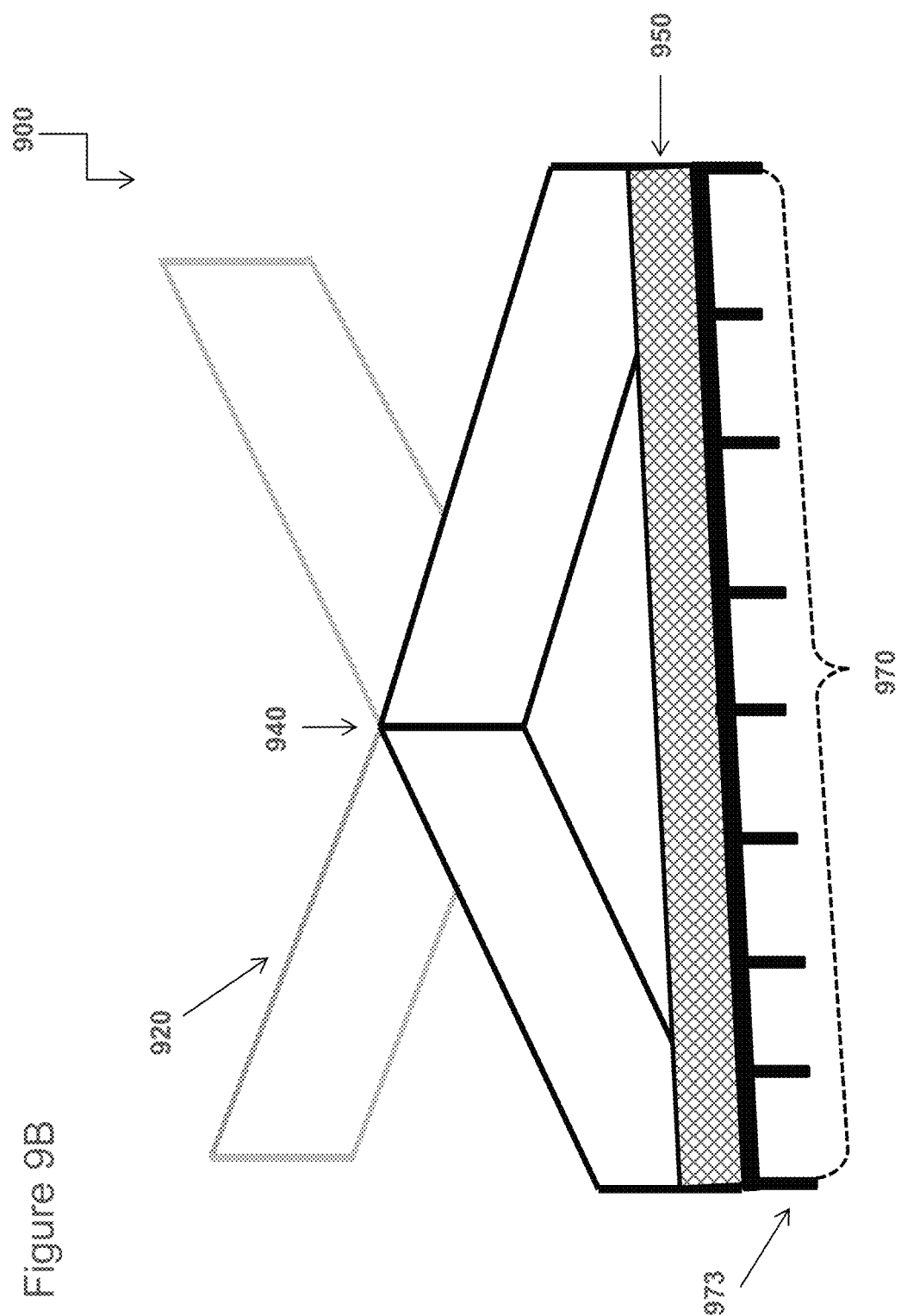
FIG. 9B illustrates an aerial view of a coupling device including a disruptor, according to a specific embodiment of the disclosure.

FIGS. 9A and 9B illustrate specific example embodiments of coupling devices 900 comprising a plurality of arms 920, a connection point 940, a support band 950, and a disruptor 970 configured to disrupt or dislodge a particulate matter (e.g., debris, dead microcrop tissue) from at least one surface (e.g., floor, peripheral wall) of a bioreactor container. As illustrated in FIG. 9A a disruptor 970 be fixedly or removable suspended from a connection point by a cord 971 (e.g., flexible, rigid). FIG. 9B illustrates an example embodiment having a disruptor fixedly or removably connected to a lower side of a support band. In some embodiments a disruptor may comprise one or more bristles 973. In some embodiments a coupling device comprising a disruptor may disrupt or dislodge a particulate matter from at least one surface of a bioreactor container as a result of a rotation of the coupling device (e.g., wind, motor function, a drive mechanism).

Methods of Cultivating a Substantially Uniformly Distributed Microcrop

The disclosure relates, in some embodiments, to a method of cultivating a substantially uniformly (e.g., uniformly) distributed microcrop (e.g., *Lemna*). For example, a method may comprise: growing a microcrop in a bioreactor system, wherein the bioreactor system comprises: (i) a bioreactor container configured to contain the microcrop (e.g., a photosynthetic aquatic species) in sufficient growth medium to permit normal growth of the microcrop, (ii) at least one coupling device comprising a star and a support band, and (iii) a fluid conveyance mechanism configured to apply sufficient force to the at least one coupling device to cause motion thereof. Motion may include motion about a fixed point on a coupling device (e.g., rotational motion), motion in the direction of flow of a microcrop (e.g., translational motion), and/or motion toward the bioreactor container (e.g., lateral motion)[or any combination thereof]. A substantially uniformly distributed microcrop, in some embodiments, may be a microcrop (e.g., *Lemna*) population having a distribution pattern across a surface of a growth medium such that a microcrop mat may have a substantially uniform thickness. A bioreactor container may contain, according to some embodiments, at least one coupling device, a growth media having an upper surface and a single microcrop population in a single mat, wherein the mat occupies the entire surface and the mat has a substantially uniform thickness. In some embodiments, a bioreactor container may contain at least one coupling device, a growth media having an upper surface and a single microcrop population in one or more mats, wherein each mat occupies less than the entire surface and each mat has a substantially uniform thickness. A bioreactor container may contain, according to some embodiments, at least one coupling device having a maximum dimension, the endpoints of which define a coupling device circumference when the coupling device is rotated in the plane of the maximum dimension, a growth media having an upper surface, and a single microcrop population, wherein each portion of the microcrop population within the coupling device circumference of the at least one coupling device has a substantially uniform thickness. A single microcrop population may have, in some embodiments, a substantially uniform thickness across the entire surface of the growth medium in the bioreactor container or across the entire surface of the portion of the growth medium in which the microcrop population is found. In some embodiments, a substantially uniform thickness exists where the difference in thickness of the microcrop at any two points is (e.g., is always) less than 5%, or less than 10%, or less than 15%, or less than 20%, or less than 25%, or less than 30%, or less than 35%, or less than 40%, or less than 50%, or less than 75%, or less than 100%. In some embodiments, a substantially uniform thickness exists where the standard deviation of the thickness of a microcrop mat is less than 0.5 mm, or less than 1 mm, or less than 2 mm, or less than 5 mm, or less than 10 mm, or less than 20 mm. In some embodiments, a substantially uniform thickness exists where neither the thinnest portion of a microcrop mat nor the thickest portion of a microcrop mat vary from the average thickness by more than 2%, or by more than 5%, or by more than 10%, or by more than 15%, or by more than 20%, or by more than 25%, or by more than 30%, or by more than 35%, or by more than 40%, or by more than 50%, or by more than 75%, or by more than 100%. The average thickness of a microcrop mat and/or population may be, in some embodiments, about 0.5 mm, or about 1 mm, or about 2 mm, or about 3 mm, or about 4 mm, or about 5 mm, or about 6 mm, or about 7 mm, or about 8 mm, or about 9 mm, or about 10 mm, or about 20 mm.

Persons skilled in the art may make various changes in the shape, size, number, separation characteristic, and/or arrangement of parts without departing from the scope of the instant disclosure. For example, the size, composition, position and number of connection points, arms, blades, and/or support bands may be varied. In addition, the size of a coupling device and/or system may be scaled up (e.g., to reduce the number for a microcrop cultivation system) or down (e.g., to enhance the wind resistance and/or microcrop piling in a system) to suit the needs and/or desires of a practitioner. According to some embodiments, a star and support band may be configured as and/or likened to a wheel with a hub (e.g., connection point), spokes (e.g., arms or blades), and a rim (e.g., support band). In some embodiments, coupling devices may be interchangeable and/or may be configured for a desired function or purpose. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. Where desired, some embodiments of the disclosure may be practiced to the exclusion of other embodiments.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100.

These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A bioreactor system for culturing a floating microcrop, the bioreactor system comprising:
    a bioreactor container configured to contain the floating microcrop in a growth medium,
    at least one coupling device configured to be sufficiently buoyant relative to the growth medium such that a cross section of the at least one coupling device is continuously positioned at or immediately below a top surface of the growth medium, the at least one coupling device comprising:
    a star having a plurality of arms joined at a connection point, and
    a fluid conveyance mechanism configured to move the growth medium and cause movement of the at least one coupling device, wherein movement of the at least one coupling device causes movement of at least a portion of the floating microcrop on the top surface of the growth medium.

2. The bioreactor system of claim 1, wherein the at least one coupling device further comprises a support band.

3. The bioreactor system of claim 2, wherein the support band comprises a material selected from wood, plastic, polystyrene, metal, a composite, a resin, a laminate, particle board, plywood mesh, chicken wire, ribbed aluminum, foam board, corrugated plastic board, woven fabric, wire, rope, string, and any combination thereof.

4. The bioreactor system of claim 1, wherein the connection point is a point in space or a hub.

5. The bioreactor system of claim 1, wherein the plurality of arms comprises a first arm joined to a second arm at the connection point.

6. The bioreactor system of claim 1, wherein the plurality of arms comprises a first arm, a second arm, a third arm, and a fourth arm joined at the connection point and spaced 90° apart.

7. The bioreactor system of claim 1, wherein the fluid conveyance mechanism further comprises a filter mechanism configured to remove at least a portion of a particulate matter from the growth medium.

8. The bioreactor system of claim 1, wherein the at least one coupling device further comprises at least one disruptor.

9. The bioreactor system of claim 1, wherein the at least one coupling device is further configured such that 100% of a cross-section of the at least one coupling device is submerged in the growth medium.

10. The bioreactor system of claim 1, wherein the at least one coupling device is further configured such that 98% of a cross-section of the at least one coupling device is submerged in the growth medium.

11. The bioreactor system of claim 1, wherein the at least one coupling device is further configured such that 50% of a cross-section of the at least one coupling device is submerged in the growth medium.

12. A method of cultivating a substantially uniformly distributed floating microcrop, the method comprising:

growing the floating microcrop in a bioreactor system, wherein the bioreactor system comprises:
- a bioreactor container configured to contain the floating microcrop in a growth medium,
- at least one coupling device configured to be sufficiently buoyant relative to the growth medium such that a cross section of the at least one coupling device is continuously positioned at or immediately below a top surface of the growth medium, the at least one coupling device comprising:
- a star having a plurality of arms joined at a connection point, and
- a fluid conveyance mechanism configured to move the growth medium and cause movement of the at least one coupling device, wherein movement of the at least one coupling device causes movement of at least a portion of the floating microcrop on the top surface of the growth medium.

13. The method of claim 12, wherein the at least one coupling device further comprises a support band.

14. The method of claim 12, wherein the connection point is a point in space or a hub.

15. The method of claim 12, wherein the plurality of arms comprises a first arm joined to a second arm at the connection point.

16. The method of claim 12, wherein the plurality of arms comprises a first arm, a second arm, a third arm, and a fourth arm joined at the connection point and spaced 90° apart.

17. The method of claim 12, further comprising removing at least a portion of a particulate matter from the growth medium using a filter mechanism of the fluid conveyance mechanism.

18. The method of claim 12, wherein the at least one coupling device further comprises at least one disruptor.

19. The method of claim 12, wherein the floating microcrop is *Lemna*.

20. The method of claim 12, wherein the at least one coupling device is further configured such that 100% of a cross-section of the at least one coupling device is submerged in the growth medium.

21. The method of claim 12, wherein the at least one coupling device is further configured such that 98% of a cross-section of the at least one coupling device is submerged in the growth medium.

22. The method of claim 12, wherein the at least one coupling device is further configured such that 50% of a cross-section of the at least one coupling device is submerged in the growth medium.

* * * * *